(12) United States Patent
Lewis et al.

(10) Patent No.: US 9,045,657 B2
(45) Date of Patent: Jun. 2, 2015

(54) VISCOELASTIC INK FOR DIRECT WRITING OF HYDROGEL STRUCTURES

(75) Inventors: Jennifer A. Lewis, Urbana, IL (US);
Robert F. Shepherd, St. Paul, MN (US);
Robert A. Barry, III, Beaverton, OR (US); Sara T. Parker, Portland, OR (US); Jennifer N. H. Shepherd, St. Paul, MN (US); Pierre Wiltzius, Santa Barbara, CA (US); Ralph G. Nuzzo, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 172 days.

(21) Appl. No.: 13/636,542

(22) PCT Filed: Mar. 22, 2011

(86) PCT No.: PCT/US2011/029429
§ 371 (c)(1),
(2), (4) Date: Nov. 28, 2012

(87) PCT Pub. No.: WO2011/119607
PCT Pub. Date: Sep. 29, 2011

(65) Prior Publication Data
US 2013/0084449 A1    Apr. 4, 2013

Related U.S. Application Data

(60) Provisional application No. 61/317,076, filed on Mar. 24, 2010.

(51) Int. Cl.
| C09D 11/16 | (2014.01) |
| A61K 9/70 | (2006.01) |
| C09D 11/10 | (2014.01) |
| A61L 27/16 | (2006.01) |
| A61L 27/26 | (2006.01) |
| A61L 27/52 | (2006.01) |
| A61L 27/56 | (2006.01) |
| C09D 11/101 | (2014.01) |

(52) U.S. Cl.
CPC ............. *C09D 11/16* (2013.01); *C09D 11/10* (2013.01); *A61L 27/16* (2013.01); *A61L 27/26* (2013.01); *A61L 27/52* (2013.01); *A61L 27/56* (2013.01); *C09D 11/101* (2013.01)

(58) Field of Classification Search
CPC ......... A61L 27/16; A61L 27/26; A61L 27/52; C09D 11/101; C09D 11/10
USPC ........................................................ 424/221
See application file for complete search history.

(56) References Cited

U.S. PATENT DOCUMENTS

| 4,321,711 A | 3/1982 | Mano ................................. 3/1.4 |
| 4,438,253 A | 3/1984 | Casey et al. ...................... 528/86 |
| 4,704,131 A | 11/1987 | Noishiki et al. ................. 623/66 |
| 4,826,945 A | 5/1989 | Cohn et al. ....................... 528/76 |
| 4,842,575 A | 6/1989 | Hoffman, Jr. et al. ........... 600/36 |
| 5,034,265 A | 7/1991 | Hoffman et al. ............... 428/253 |
| 5,202,413 A | 4/1993 | Spinu ............................ 528/354 |
| 5,306,311 A | 4/1994 | Stone et al. ...................... 623/18 |
| 5,410,016 A | 4/1995 | Hubbell et al. ................ 528/354 |
| 5,415,619 A | 5/1995 | Lee et al. ......................... 600/36 |
| 5,529,914 A | 6/1996 | Hubbell et al. ................ 435/182 |
| 5,567,440 A | 10/1996 | Hubbell et al. ................ 424/484 |
| 5,573,934 A | 11/1996 | Hubbell et al. ................ 435/177 |
| 5,584,875 A | 12/1996 | Duhamel et al. .................. 623/1 |
| 5,843,160 A | 12/1998 | Rhodes ............................. 623/1 |
| 5,854,382 A | 12/1998 | Loomis ......................... 528/354 |
| 6,514,515 B1 | 2/2003 | Williams ....................... 424/424 |
| 7,141,617 B2 * | 11/2006 | Gratson et al. ................ 523/160 |
| 2005/0008675 A1 | 1/2005 | Bhatia et al. .................. 424/426 |
| 2010/0158880 A1 * | 6/2010 | Seyda et al. ................ 424/93.21 |

FOREIGN PATENT DOCUMENTS

WO    WO 2008/069915 A2    6/2008    ............. A61B 17/04

OTHER PUBLICATIONS

Nguyen, Kytai T. et al. Photopolymerizable hydrogels for tissue engineering applications. 2002. Biomaterials. pp. 4307-4314.*
Moore et al. Immobilized Concentration Gradients of Neurotrophic Factors Guide Neurite Outgrowth of Primary Neurons in Macroporous Scaffolds. Tissue Engineering. vol. 12, No. 2. 2006. pp. 267-278.*
Brewer, Gregory J., "Isolation and Culture of Adult Rat Hippocampal Neurons," *Journal of Neuroscience Methods* 71 (1997) pp. 143-155.
Clark, Peter et al., "Growth Cone Guidance and Neuron Morphology on Micropatterned Laminin Surfaces," *Journal of Cell Science* 105 (1993) pp. 203-212.
Cukierman, Edna et al., "Taking Cell-Matrix Adhesions to the Third Dimension," *Science* 294 (2001) pp. 1708-1712.
Duoss, et al., "Sol-Gel Inks for Direct-Write Assembly of Functional Oxides," *Advanced Materials* 19 (2007) pp. 3485-3489.
Friedl, Peter et al., "Cell Migration Strategies in 3-D Extracellular Matrix: Differences in Morphology, Cell Matrix Interactions, and Integrin Function," *Microscopy Research and Technique* 43 (1998) pp. 369-378.
Ghosh, Sourabh et al., "Direct-Write Assembly of Microperiodic Silk Fibroin Scaffolds for Tissue Engineering Applications," *Advanced Functional Materials* 18 (2008) pp. 1883-1889.
Gratson, Gregory M. et al., "Direct Writing of Three-Dimensional Webs," *Nature* 428 (2004) p. 386.

(Continued)

*Primary Examiner* — Frederick Krass
*Assistant Examiner* — Tracy Liu
(74) *Attorney, Agent, or Firm* — Brinks Gilson & Lione

(57) ABSTRACT

A viscoelastic ink for direct writing of hydrogel structures includes a long chain polymer and a photopolymerizable moiety, which may be a photopolymerizable monomer or a photopolymerizable group attached to the long chain polymer. The ink may also include a crosslinking agent, a photoinitiator, and water. The long chain polymer is present at a concentration greater than a critical overlap concentration c* of the long chain polymer in the ink.

19 Claims, 20 Drawing Sheets

(56) References Cited

OTHER PUBLICATIONS

Gratson, Gregory M. et al., "Phase Behavior and Rheological Properties of Polyelectrolyte Inks for Direct-Write Assembly," *Langmuir* 21 (2005) pp. 457-464.

Hanson, Jennifer N. et al., "Textural Guidance Cues for Controlling Process Outgrowth of Mammalian Neurons," *Lab on a Chip* 9 (2009) pp. 122-131.

Hindié, M. et al., "Interactions of B16F10 Melanoma Cells Aggregated on a Cellulose Substrate," *Journal of Cellular Biochemistry* 99 (2006) pp. 96-104.

Irons, Hillary R. et al., "Three-Dimensional Neural Constructs: A Novel Platform for Neurophysiological Investigation," *Journal of Neural Engineering* 5 (2008) pp. 333-341.

Kam, L. et al., "Axonal Outgrowth of Hippocampal Neurons on Micro-Scale Networks of Polylysine-Conjugated Laminin," *Biomaterials* 22 (2001) pp. 1049-1054.

Langer, Robert et al., "Tissue Engineering," *Science* 260 (1993) pp. 920-926.

Lee, Jung Woo et al., "Three-Dimensional Cell Culture Matrices: State of the Art," *Tissue Engineering: Part B* 14, 1 (2008) pp. 61-87.

Luo, Ying et al., "A Photolabile Hydrogel for Guided Three-Dimensional Cell Growth and Migration," *Nature Materials* 3 (2004) pp. 249-253.

Mesfin-Dowell, N.M. et al., "Topographically Modified Surfaces Affect Orientation and Growth of Hippocampal Neurons," *Journal of Neural Engineering* 1 (2004) pp. 78-90.

Offenhäusser, Andreas et al., "Microcontact Printing of Proteins for Neuronal Cell Guidance," *Soft Matter* 3 (2007) pp. 290-298.

Pedersen, John A. et al., "Mechanobiology in the Third Dimension," *Annals of Biomedical Engineering* 33, 11 (2005) pp. 1469-1490.

Rajnicek, Ann M. et al., "Contact Guidance of CNS Neurites on Grooved Quartz: Influence of Groove Dimensions, Neuronal Age and Cell Type," *Journal of Cell Science* 110 (1997) pp. 2905-2913.

Ray, Jasodhara et al., "Proliferation, Differentiation, and Long-Term Culture of Primary Hippocampal Neurons," *Proc. Natl. Acad. Sci. USA* 90 (1993) pp. 3602-3606.

Schindler, Melvin et al., "Living in Three Dimensions—3D Nanostructured Environments for Cell Culture and Regenerative Medicine," *Cell Biochemistry and Biophysics* 45 (2006) pp. 215-227.

Schmidt, Christine E. et al., "Neural Tissue Engineering: Strategies for Repair and Regeneration," *Annual Review of Biomedical Engineering* 5 (2003) pp. 293-347.

Seidlits, Stephanie K. et al., "High Resolution Patterning of Hydrogels in Three Dimensions Using Direct-Write Photofabrication for Cell Guidance," *Advanced Functional Materials*, 19 (2009) pp. 3543-3551.

Tayalia, Prakriti et al., "3D Cell-Migration Studies Using Two-Photon Engineered Polymer Scaffolds," *Advanced Materials* 20 (2008) pp. 4494-4498.

Vozzi, G. Ph.D. et al., "Microsyringe-Based Deposition of Two-Dimensional and Three-Dimensional Polymer Scaffolds with a Well-Defined Geometry for Application to Tissue Engineering" *Tissue Engineering* 8, 6 (2002) pp. 1089-1104.

Willerth, Stephanie M. et al., "Optimization of Fibrin Scaffolds for Differentiation of Murine Embryonic Stem Cells into Neural Lineage Cells" *Biomaterials* 27 (2006) pp. 5990-6003.

Parker, Sara T. et al., "Direct-Write Assembly of 3D Microperiodic Hydrogel Scaffolds for Tissue Engineering Applications," *Materials Research Society* (*MRS*) Fall Meeting, Boston MA, Dec. 1, 2008.

\* cited by examiner

VISCOELASTIC INK FOR DIRECT WRITING OF HYDROGEL STRUCTURES

RELATED APPLICATIONS

The present patent document is the national stage of International Application No. PCT/US2011/029429, which was filed on Mar. 22, 2011, and which claims the benefit of the filing date under 35 U.S.C. §119(e) of U.S. Provisional Patent Application Ser. No. 61/317,076, which was filed on Mar. 24, 2010, both of which are hereby incorporated by reference in their entirety.

FEDERALLY SPONSORED RESEARCH OR DEVELOPMENT

The subject matter of the present disclosure was supported by the Wm. Keck Foundation, Nanoscale Chemical-Electrical-Mechanical Manufacturing Systems (contract no. DMI-0328162), National Science Foundation (contract no. CHE-07-4153), U.S. Army Research Office (contract no. DAAD19-03-1-0227) and the National Institutes of Health (contract nos. MH085220 and R01 EY01736-01A1). The government has certain rights in the invention.

TECHNICAL FIELD

The present disclosure is related generally to polymer-based ink systems and more particularly to viscoelastic ink systems employed for direct ink writing of hydrogel structures.

BACKGROUND

Three-dimensional structures with micron-scale features have many potential applications, including photonic band gap materials, tissue engineering scaffolds, biosensors, and drug delivery systems. Consequently, several assembly techniques for fabricating complex three-dimensional structures with features smaller than 100 microns have been developed, such as microfabrication, holographic lithography, two-photon polymerization and colloidal self-assembly. However, all these techniques have limitations that reduce their utility.

Two-photon polymerization is capable of creating three-dimensional structures with sub-micron features, but from precursors that are not biocompatible and at a very slow rate, ca.<10 µm/s. Many techniques have been developed to fabricate three-dimensional photonic crystals, but they rely on expensive, complicated equipment or time-consuming procedures. Colloidal self-assembly has also been utilized to make three-dimensional periodic structures, but controlling the formation of defects is difficult.

Polymeric solutions are used in nature to fabricate thin filaments. Spiders, for example, derive their silk fibers from a concentrated protein biopolymer solution that solidifies as it is drawn to form an extremely strong filament. The extensional flow of the solution aligns liquid crystal sheets in the polymer, and the solution gels by adding ions as it leaves the spinneret. This process may be artificially recreated by the deposition of the recombinant spider silk biopolymer into a polar "deposition bath" to produce filament fibers with comparable properties.

Hydrogels are an important class of soft materials that can be fabricated in the form of three-dimensional (3D) microperiodic structures by colloidal templating or interference lithography. However, neither approach allows one to omnidirectionally vary the spacing between patterned features over length scales ranging from sub-micrometer to tens of micrometers.

The ability to pattern soft materials at the microscale is critical for several emerging technologies, including tissue-engineering scaffolds, photonic crystals, sensors, and self-healing materials. Tissue-engineering scaffolds are typically composed of synthetic or natural polymers and provide a means for tissue to grow outside the body. The scaffolds may be biodegradable or non-biodegradable. A challenge in the field is to select or design a scaffold material for cell growth and differentiation that has desirable properties, including mechanical strength, durability, and biocompatibility, and which does not induce an immune response.

BRIEF SUMMARY

A viscoelastic ink for direct writing of hydrogel structures and an improved hydrogel scaffold are described, and a method of making the hydrogel scaffold is also set forth. Several model ink systems are shown to have excellent 3D-writing capabilities and also cytocompatibility with several types of cells, including mouse 3T3 fibroblasts, rat primary hippocampal neurons and human primary embryonic stem cells. The ability to create hydrogel scaffolds with microscale features in both planar and 3D forms may open a new avenue for tailoring scaffolds for tissue engineering and other applications.

The viscoelastic ink includes a long chain polymer and a photopolymerizable moiety, which may be a photopolymerizable monomer or a photopolymerizable group attached to the long chain polymer. The ink may also include a crosslinking agent, a photoinitiator, and water. The long chain polymer is present at a concentration above a critical overap concentration c* of the long chain polymer in the ink. For example, the concentration of the long chain polymer may be 5-100 times greater than the critical overlap concentration c*.

The hydrogel scaffold includes a framework of interconnected rods arranged in one or more layers, where the rods are defined by one or more hydrogel filaments. Each layer of the framework includes a spacing between adjacent rods of between about 1 micron and about 100 microns. The one or more hydrogel filaments have a pre-polymerized structure and a post-polymerized structure, where the post-polymerized structure comprises a shear elastic modulus $G'_2$ at least two orders of magnitude greater than a shear elastic modulus $G'_1$ of the pre-polymerized structure.

The method includes forming an ink comprising a long chain polymer and a photopolymerizable moiety, extruding the ink through a micronozzle to form an extruded filament, photopolymerizing the extruded filament; and depositing the extruded filament in a pattern on a substrate to form a hydrogel scaffold. The photopolymerization may be carried out before or after deposition of the extruded filament on the substrate.

DETAILED DESCRIPTION

Viscoelastic "inks" designed to have dynamic and mechanical properties suited for printing three-dimensional (3D) hydrogel architectures are described herein. Using direct ink writing, the viscoelastic inks may be applied to a substrate to create planar or 3D hydrogel scaffolds of predetermined dimensions, geometry, and microperiodicity. Direct ink writing is a layer-by-layer assembly technique that allows scaffolds to be formed with lateral feature sizes that are at least an order of magnitude smaller than those achieved by ink-jet printing and other rapid prototyping approaches and nearly comparable in size to those produced by two-photon polymerization and interference holography.

Central to the approach is the creation of concentrated inks that can be extruded through fine deposition nozzles in filamentary form and which undergo rapid solidification to maintain their shape even as they span gaps in the underlying layer(s). Unlike prior efforts on polyelectrolyte inks that required reservoir-induced coagulation to enable 3D printing, the inventive viscoelastic inks can be printed directly in air, where they undergo solidification via photopolymerization. The resulting hydrogel scaffolds may be tailored for use as tunable optical sensors, stimuli-responsive soft materials, and tissue engineering scaffolds. For tissue engineering applications, the hydrogel scaffolds may be dissolved in vivo or chemically cross-linked to provide permanent cellular support.

Figure 1A:
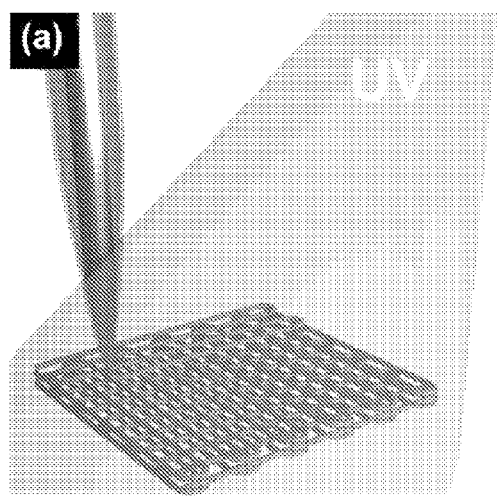
FIG. 1(a) is a schematic illustration of direct writing of a hydrogel-based ink through a gold-coated deposition micronozzle that is simultaneously photopolymerized via ultraviolet (UV) illumination.
Figure 1B:
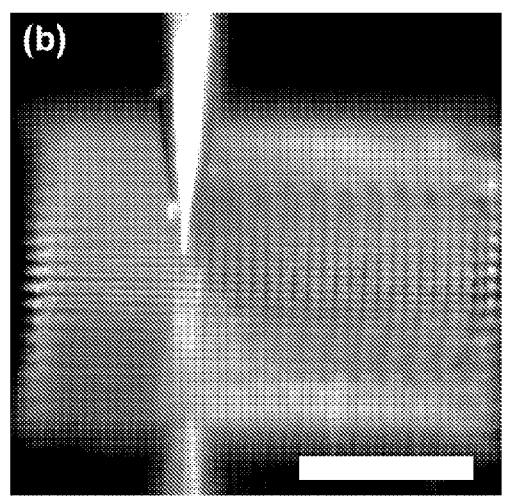
FIG. 1(b) is an optical image of a 3D hydrogel scaffold acquired during direct ink writing (scalebar is 200 µm)

A direct ink writer that includes a 3-axis micropositioning stage and a syringe for housing the ink mounted on the micropositioning stage may be employed to form the hydrogel scaffolds. Referring to FIGS. 1(a) and 1(b), the ink is extruded through the tip of a tapered micro-capillary nozzle to form a hydrogel filament that is deposited onto a stationary substrate (e.g., a glass substrate). The extrusion occurs at a predetermined pressure and deposition speed. After patterning the initial layer, the nozzle is incrementally raised in the z-direction to generate the next layer. This process is repeated until the desired 3D structure is formed. 3D periodic scaffolds composed of a simple tetragonal geometry, for example, can be assembled by patterning an array of parallel filaments in the x-y plane such that their orientation is orthogonal to the layers immediately above and below a given layer. Photocuring with ultraviolet (UV) light may be carried out as the filament exits the nozzle or after deposition of the filament on the substrate.

The viscoelastic inks extruded through the micronozzle preferably include a long chain polymer and a photopolymerizable moiety, which may be a photopolymerizable monomer or a photopolymerizable group attached to the long chain polymer. The inks may also include a crosslinking agent, a photoinitiator, and water. The long chain polymer is present at a concentration in the ink sufficient to be physically entangled, that is, at a concentration well above the dilute-to-semidilute transition c* of the long chain polymeric species in the ink, where $$c^* = \frac{M_w}{4/3\pi R_g^3 N_A},$$

$M_w$=polymer molecular weight, $R_g$=radius of gyration of the polymer chains in solution, and $N_A$=Avogadro's number. For example, the concentration of the long chain polymer may be at least about 5 times greater than the critical overlap concentration c*, or at least about 10 times greater than the critical overlap concentration c*. The concentration of the long chain polymer may also be at least about 100 times greater than the critical overlap concentration c*.

The long chain polymer may be, for example, polyacrylamide (pAM), poly(2-hydroxyethyl methacrylate) (pHEMA), poly(hyaluronic acid) (pHA), poly(N-isopropylacrylamide) (PNIPAAm), poly(ethylene oxide)/polyethylene glycol diacrylate, poly(vinyl alcohol), PLA/PGA/PLGA, block copolymers such as poloxamers (e.g., Pluronics®), polyphosphazene, alginate derivatives, or collagen derivatives. Generally, the concentration of the long chain polymer in the ink is about 5 wt. % or greater, about 10 wt. % or greater, or about 20 wt. % or greater. For example, the concentration may lie between about 5 wt. % and about 50 wt. % depending on the molecular weight of the long chain polymer.

The viscoelastic inks may include a photopolymerizable monomer, such as monomeric acrylamide or hydroxyethyl methacrylate in the case of inks based on pAM or pHEMA, respectively. During photocuring, the monomer forms a chemically crosslinked polymer network that penetrates the physically entangled polymer chains. The monomer may be present in the ink at a concentration in the range of from about 25 wt. % to about 55 wt. %. Other inks, such as those based on pHA, may include long chains of the polymer chemically modified with photopolymerizable groups (e.g., methacrylate groups) that allow the chains to participate in the crosslinking when photocured.

The long chain polymer generally comprises polymer chains having a molecular weight of at least about 300,000. The molecular weight may also be at least about 500,000. The long chain polymer may include a multimodal (e.g., bimodal) distribution of molecular weights. For example, the long chain polymer may include first polymer chains having a first molecular weight (e.g., in the range from about 300,000 to about 500,000) and second polymer chains having a second molecular weight (e.g., in the range of from about 1,000,000 to about 1,500,000). The concentration of the first polymer chains in the ink may be the same as or different from that of the second polymer chains. For example, as discussed further below in reference to an exemplary pHEMA ink system, the concentration of the first polymer chains in the ink, which have a molecular weight of 300,000, may be higher than the concentration of the second polymer chains, which have a molecular weight of 1,000,000. In this exemplary system, the concentrations are 25 wt. % and 10 wt. % for the first and second polymer chains, respectively.

By varying the pressure and deposition speed of the direct writing process, a given viscoelastic ink may be used with a variety of nozzle diameters. Typically, the ink is extruded through the micro-capillary nozzle under an applied pressure of between about 60 kPa and about 600 kPa at a deposition speed ranging from about 50 $\mu$m·s$^{-1}$ to about 500 $\mu$m·s$^{-1}$. For example, the applied pressure may be between about 100 kPa and about 500 kPa, or between about 200 kPa and about 400 kPa, and the deposition speed may range from about 100 $\mu$m·s$^{-1}$ to about 400 $\mu$m·s$^{-1}$, or from about 200 $\mu$m·s$^{-1}$ to about 300 $\mu$m·s$^{-1}$. The micro-capillary nozzle generally has a tip diameter ranging from about 1 micron to about 100 microns in size. For example, the nozzle (tip) diameter may be between about 1 micron and about 50 microns, or between about 5 microns and about 10 microns. Accordingly, the ink may be extruded through the micronozzle at a shear rate of at least about 10 s$^{-1}$, or at least about 100 s$^{-1}$. Due to the viscoelastic nature of the polymers, the ink exhibits a high viscosity at a low shear rate (e.g., about 0.1 s$^{-1}$ or less) and a substantially reduced viscosity during the extrusion through the micronozzle. The viscosity may reduced by an order of magnitude or more during the extrusion, a phenomenon referred to as "shear-thinning" behavior. For example, the viscosity of the ink during extrusion may be about 20 Pa·s or less compared to about 1,000 Pa·s at a low shear rate.

The extruded filament(s) are patterned to form the hydrogel scaffold, which may have a single or multilayer structure made up of interconnected rods. The rods typically have a width (or diameter) in the range of from about 1 micron to about 10 microns and a spacing (or pitch) in the range of from about 5 microns to about 100 microns. For example, the pitch may be between about 1 micron and about 100 microns, between about 10 microns and about 80 microns, or between about 20 microns and about 60 microns. Generally, scaffolds formed by direct ink writing include from 1 to 20 or more layers. The scaffold may be periodic in one dimension, in two dimensions, or in three dimensions.

Due to the in-situ or post-deposition photocuring step, the extruded hydrogel filament has a pre-polymerized structure and a post-polymerized structure, each of which may have different elastic properties. The pre-polymerized structure of the hydrogel filament includes a physically entangled polymer network with no chemically crosslinked polymer chains. This physical gel structure exhibits elastic and viscous behavior that is well suited for extrusion through the micronozzle. In contrast, the post-polymerized structure of the hydrogel filament may include a physically entangled polymer network and a chemically crosslinked polymer network. For example, an ink including a long chain polymer as well as a photopolymerizable monomer may be transformed by photocuring to have an interpenetrating physical and chemical gel structure. Alternatively, the post-polymerized structure may include a chemically crosslinked polymer network with no physically entangled polymer chains. This structure may result from photocuring of an ink containing a physically entangled long chain polymer that has been chemically modified to include photopolymerizable groups along its backbone; as a result, the long chain polymer itself participates in the cross-linking and the physical gel structure is transformed to a chemical gel structure during photocuring. It is also possible for the post-polymerized structure of the hydrogel filament to include only a physically entangled polymer network with no chemical crosslinks. In this case, the elastic properties of the starting sol-gel ink and the extruded hydrogel filament may be similar, and relatively weak scaffolds may be prepared. Such scaffolds may be ideal for differentiation of primary stem cells into neuronal cells, for example.

For other scaffold applications, however, it may be advantageous for the post-polymerized structure of the hydrogel filament(s) to exhibit a shear elastic modulus $G'_2$ that is at least two orders of magnitude greater than the shear elastic modulus $G'_1$ of the pre-polymerized structure. The shear elastic modulus $G'_2$ may also be at least three orders of magnitude greater than the shear elastic modulus $G'_1$. Such an increase in the stiffness of the filaments prevents or minimizes deformation (e.g., sagging or collapse) of the resulting hydrogel scaffold. This enhanced stiffness may be obtained from polymerized hydrogel filaments that include either or both physically entangled and chemically cross-linked polymer chains, as supported by various elasticity data described below.

Typically, UV radiation having a wavelength in the range of from 250 nm to 400 nm is employed for photopolymerization, and the intensity of the radiation generally lies in the range of from about 50 mW/cm$^2$ to about 400 mW/cm$^2$. Alternatively, the ink may be polymerized by another means (e.g., chemicals, heat, etc.)

After polymerization, the hydrogel scaffold may be chemically treated (if needed) to render the scaffold compliant for tissue growth. For example, the hydrogel scaffold may be immersed in a polylysine solution. Then, cells such as 3T3 murine fibroblasts, primary rat hippocampal neurons and human embryonic stem cells may be plated onto one-, two- and four-layer hydrogel scaffolds, as described below, to demonstrate their biocompatibility and potential suitability for tissue engineering applications.

Polyacrylamide (pAM) Based Ink System

One approach to creating a viscoelastic pAM ink includes first mixing monomeric acrylamide, glycerol, and water. Upon ageing for several hours under ambient conditions, the monomeric species polymerize to yield a gel composed of 30 wt. % polyacrylamide. (Alternatively, high molecular weight polyacrylamide chains can be mixed directly with monomer to create the ink.) $^1$HNMR reveals that peaks associated with acrylamide, which are present initially, disappear after polymerization, followed by the emergence of two new peaks that correspond to alkyl chains (data not shown). Concomitantly, as the solution ages, sharp rises in both the shear elastic, G', and loss, G'', moduli are observed, suggesting that the resulting gel is composed of physically entangled, polyacrylamide chains (see FIG. 2(a)). To determine their degree of polymerization, N, the intrinsic viscosity, $[\eta]_0$, of diluted polymer solutions is measured by capillary viscometry and found to be $[\eta]_0 \approx 270$ ml gm$^{-1}$ (see FIG. 2b). Using the Mark-Houwink relation, $[\eta]_0=KM^a$, their molecular weight is determined to be $8.9 \times 10^5$ gm mol$^{-1}$, where K is $9.3 \times 10^{-3}$ and a is taken to be 0.75 for polyacrylamide dissolved in an aqueous solution (0.5 M NaCl). Hence, this initial polymerization process yields polyacrylamide chains with an average degree of polymerization, $N=1.3 \times 10^4$, that is well above the entanglement value of $N_e=128$.

To further optimize the ink for direct-write assembly, this polymerized mixture is diluted by adding monomeric acrylamide, a crosslinking agent, N,N methylene bisacrylamide, a photoinitiator, diethoxyacetophenone, and deionized water at weight ratios (w/w) of 0.480, 0.036, 0.004, and 0.480, respectively. As noted above, the initial polymerization step could be eliminated simply by adding high molecular weight polyacrylamide chains (~10$^6$ g/mol) directly to this photopolymerizable solution.

Figures 2A, 2B, 2C, 2D:
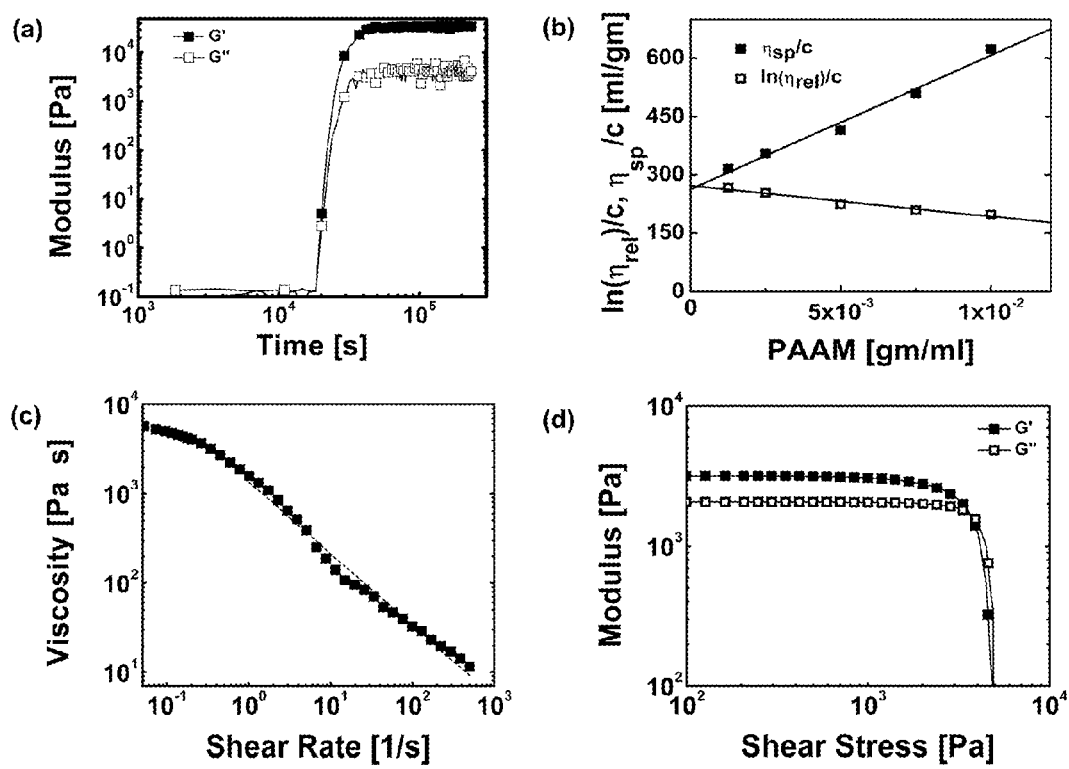
FIG. 2(a) shows shear elastic (G') and loss (G') moduli as a function of polymerization time for an exemplary ink composed of acrylamide, glycerol, and water.
FIG. 2(b) shows specific and relative viscosity of dilute polymer solutions of varying polyacrylamide (pAM) concentration.
FIG. 2(c) shows apparent viscosity as a function of shear rate for the final pAM hydrogel-based ink.
FIG. 2(d) shows shear elastic and loss moduli as a function of shear stress for the final pAM hydrogel-based ink.

The final ink formulation exhibits pronounced shear thinning behavior, which facilitates its flow through fine deposition nozzles (see FIG. 2(c)). For example, when the ink is printed through a 5 µm nozzle at 0.5 mm s$^{-1}$, which corresponds to an estimated shear rate of 100 s$^{-1}$, its viscosity is approximately 10 Pa·s. Under these conditions, the ink viscosity is nearly three orders of magnitude smaller than that observed at low shear rates 0.1 s$^{-1}$). Upon diluting the ink, its shear elastic modulus decreases by about an order of magnitude to ~3×10$^3$ Pa relative to its initial state (see FIG. 2(d)). Although this elasticity is sufficient for patterning 3D microperiodic scaffolds, the printed ink filament is advantageously further stiffened to prevent subsequent deformation, which occurs when the build times exceed several minutes. To obviate this, the direct writing process may be modified by mounting a fiber optic guide onto the printhead, which facilitates in-situ photopolymerization of the ink after it exits the gold-coated micronozzle (see FIG. 1(a)). Note, the metallic coating prevents the ink from prematurely cross-linking within the glass nozzle due to UV illumination, thereby avoiding clogging during the printing process.

Figures 3A, 3B, 3C:
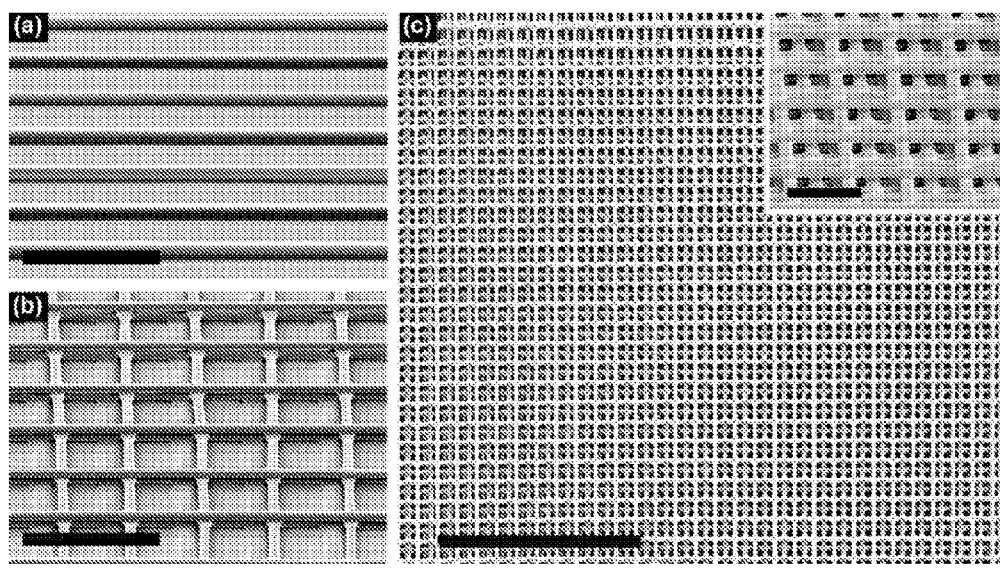
FIG. 3(a) is a scanning electron micrograph of a 1D pAM scaffold composed of 5 μm filaments with a 20 μm center-to-center spacing.
FIG. 3(b) is a 3D micro-periodic pAM hydrogel scaffold (4-layers) composed of 5 μm filaments with a 20 μm center-to-center spacing.
FIG. 3(c) is a 3D micro-periodic pAM hydrogel scaffold (6-layers) composed of nominally 1 μm filaments with a 5 μm center-to-center spacing (Note: Inset in 3(c) shows a higher magnification, tilted view of this scaffold and the scalebars are 50 μm (a-c), and 6 μm (inset), respectively)

Using this modified DIW process, hydrogel scaffolds with precisely defined filament diameter, spacing, number of layers, and geometry may be patterned. As a first example, hydrogel scaffolds composed of 5 µm filaments with a 20 µm spacing between filaments with 1-4 layers and a total area of 5 mm$^2$ (see. FIG. 3(a) and FIG. 3(b)) are created. To further demonstrate the capability of this approach, hydrogel scaffolds are printed with nominally 1 µm filaments with 5 µm spacing between filaments and 6 layers with a total area of 1 mm$^2$, as shown in FIG. 3(c). In this case, the hydrogel scaffolds are patterned in a face-centered tetragonal structure, in which the individual filaments are observed to span distances approximately five times their diameter with minimal deflection (see FIG. 3(c), inset).

Figures 4A, 4B, 4C, 4D:
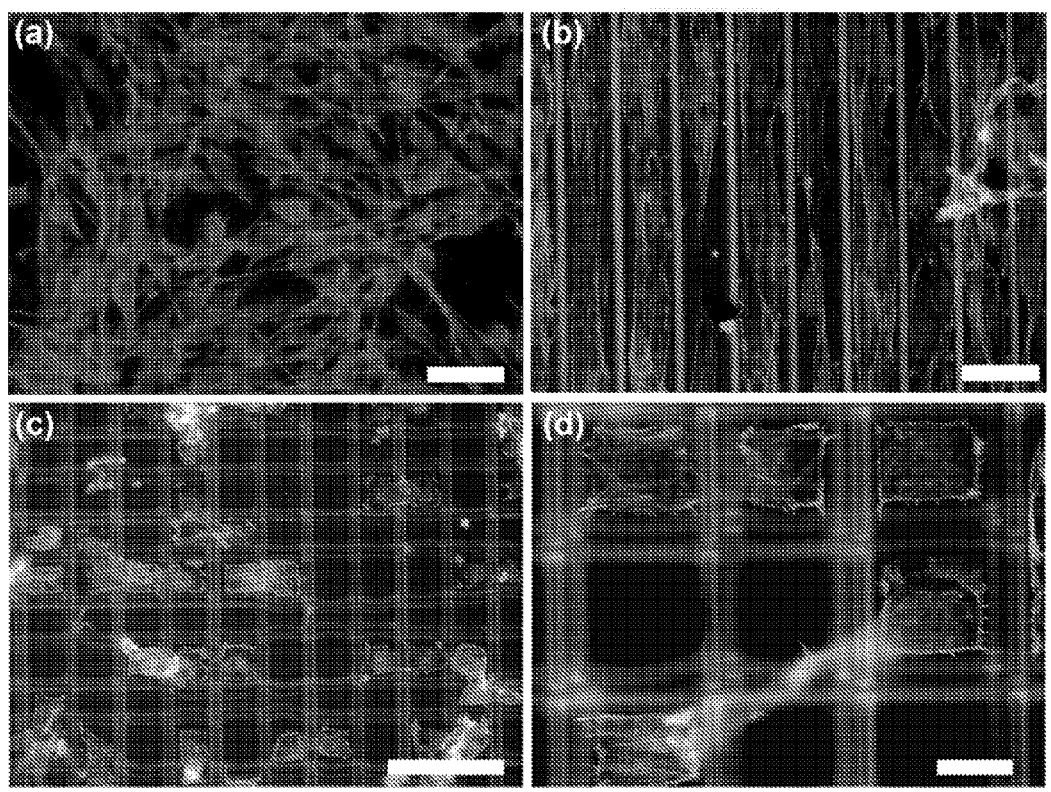
FIGS. 4(a)-4(c) are optical fluorescence micrographs of 3T3 fibroblasts plated on the 4(a) flat glass control, 4(b) 1D microperiodic pAM hydrogel scaffold, and 4(c,d) 3D microperiodic pAM hydrogel scaffolds (4-layers)
FIG. 4(d) is a higher magnification view of 4(c) demonstrating the interaction between neighboring cells, where rhodamine-phalloidin stains the actin red, DAPI stains the (DNA) nucleus blue, and the hydrogel scaffolds fluoresce green through the incorporation of fluorescein-o-acrylate (scalebars are 100 μm (a-c) and 20 μm (d), respectively)

To determine the suitability of the scaffolds for tissue engineering applications, 3T3 murine fibroblast cells are plated onto a flat glass substrate (control) as well as 1D and 3D microperiodic hydrogel scaffolds. Poly-d-lysine is absorbed into the hydrogel scaffold network prior to cell seeding to enhance their cytocompatibility. The fibroblasts plated on the control substrate display the typical flattened out morphology of cells typically seen in planar in vitro cultures, as shown in FIG. 4(a). By contrast, cell interactions with patterned features and the underlying glass substrate result in their alignment along the patterning direction of the 1D microperiodic hydrogel scaffolds, as shown in FIG. 4(b). This type of elongated morphology is similar to that observed by Zhang, et al. (S. Zhang et al., *Biomaterials*, 1999, 20, 1213) in which murine fibroblasts formed aligned cell arrays on 1D periodic patterned surfaces that were biofunctionalized by microcontact printing of a self-assembling oligopeptide monolayer. In the present investigation, atypical fibroblast morphology was observed in response to the 3D microperiodic hydrogel scaffolds (see FIGS. 4(c) and 4(d)), in which fibroblast cells integrate themselves into the regions between interconnecting hydrogel filaments. Typically one, or at most two, cell(s) reside in this space between filaments, essentially compartmentalizing themselves. It appears that the cells tend to sit in the square well created by interconnected filaments and then grow down into the scaffold towards the underlying glass substrate. Additionally, when the fibroblasts are in neighboring compartments, interactions between the filaments of adjacent fibroblast cells are observed (see FIG. 4(d)).

Material System:

The ink is initially formed by mixing 1 ml deionized water (Milli-Q, Millipore), 5 g of glycerol (Sigma Aldrich) and 3.5 g acrylamide (Acros). These constituents are magnetically stirred at 30° C. until the acrylamide fully dissolves. In the quiescent state, this solution undergoes spontaneous polymerization within hours to days. If the polymerization is slow, 0.1 M MgCl$_2$ can be added as a catalyst. After this process is complete, 2 ml of deionized water (Milli-Q, Millipore) are added to this highly viscous solution. A separate solution is produced by mixing 5 ml deionized water (Milli-Q, Millipore), 5 g acrylamide (Acros), 0.3 g methylene bisacrylamide (MP Biomedicals), 0.04 ml diethoxyacetophenone (Acros), and 0.018 g Fluorescein O-acrylate (Sigma Aldrich). 2 ml of this second solution are added in 0.5 ml aliquots to polymerized solution until the desired rheological properties are attained. Note, the fluorescently-labeled monomor is incorporated to facilitate direct imaging of the patterned scaffolds after cell culture is complete.

NMR Analysis:

$^1$HNMR measurements are carried out on a Varian Unity 400. The sample is prepared identically to the initial ink formulation; however D$_2$O is substituted for deionized water to generate an improved signal with better alignment. Specifically, 1 ml D$_2$O, 5 g of glycerol (Sigma Aldrich) and 3.5 g acrylamide (Acros) are mixed together in solution. These constituents are magnetically stirred at 30° C. until the acrylamide fully dissolves. Samples are analyzed prior to and post polymerization with NUTS (Acorn NMR) software package.

Ink Rheology:

Oscillatory rheometry is performed on the initial ink solution using a cup and bob geometry at a frequency of 1 Hz and shear stress of 1 Pa. Oscillatory rheometry is also performed on the final ink mixture at 1 Hz at a shear rate range from 0 to 200 s$^{-1}$ to determine the elastic modulus (G'), loss modulus (G'), and yield stress ($\tau_y$) of the printable ink. Viscometry is performed on the final ink mixture, from shear rates of 0 to 200 s$^{-1}$. All data is taken using a cup and bob geometry (C15; Bohlin) with 3 cc of material on a Bohlin CVOR controlled-stress rheometer.

Capillary rheology is performed by first dissolving the initial ink solution after polymerization is completed in water and then precipitating the polyacrylamide by immersion in ethanol. The monomeric acrylamide and glycerol are soluble in ethanol, while poly(acrylamide) is not. This process is repeated several times while concomitantly ultrasonicating the solution to facilitate dissolution. The precipitated polymer is then dissolved at varying concentrations in an aqueous solution containing 0.50 M NaCl. The relative and specific viscosities of these diluted polymer solutions are then measured, as a function of flow time, in an Ubbelholde viscometer in a constant temperature bath held at 26.5±0.2° C. The intrinsic viscosity is determined by measuring the flow values at different concentrations and using both the Huggins (Eq. 1) and Kraemer (Eq. 2) relationships:

$$\frac{\eta - \eta_s}{\eta_s c} = [\eta] + k_H [\eta]^2 c \qquad (1)$$

$$\frac{\ln(\eta/\eta_s)}{c} = [\eta] + \left(k_H - \frac{1}{2}\right)[\eta]^2 c \qquad (2)$$

where $\eta_s$ is the solvent viscosity, $\eta$ is the apparent viscosity, c is the polymer concentration, and $k_H$ is the Huggins coefficient. By extrapolating these equations to c=0, the intrinsic viscosity is determined.

Direct-Write Asssembly of Hydrogel Scaffolds:

Micropipette tips (World Precision Instruments) with diameters ranging from 1 to 10 μm are coated with a thin gold film (200 nm thick) to prevent photopolymerization of the ink prior to exiting the deposition nozzle. The micropipettes are mounted onto a rotating holder to ensure an even coverage and coated inside a metal evaporator (Denton Vacuum DV-5024). Coverslip substrates are cleaned in piranha (sulfuric acid, hydrogen peroxide) solution for 1 h, rinsed with deionized water, and dried with nitrogen. Coverslips are placed in a 98% toluene (Fisher Scientific), 2% 3-(trimethoxysilyl)propyl methacrylate (Acros) solution for 18 hours at 60° C. The slides are removed just prior to drawing, rinsed with isopropanol, and dried. The ink is loaded into a syringe, with an attached gold-coated tip in place. Once the substrate is leveled, ink flow is initiated by applying a pressure of 70-80 psi. After the flow has begun, the pressure is reduced to 20-30 psi and the patterning is initiated. The printed scaffolds are defined by filament width, spacing between filaments, total patterned area, number of layers, and their geometry. We create both planar and 3D scaffolds with 1 to 5 μm filaments and a 5 to 20 μm spacing between filaments over 5 mm$^2$ areas with 1-6 layers. A UV lamp (Omnicure S200; Exfo), with a λ=320 nm-400 nm, is used to expose the patterned structure to 5 mW/cm$^2$ during the deposition process. Once patterning is complete, the scaffolds are exposed to a higher intensity UV light source, ~400 mW/cm$^2$, for 20 min to ensure a fully photo-cured structure. To drive off excess water and enhance scaffold rigidity, each scaffold is then heated to 100° C. for 18 hours.

Scaffold Imaging:

The printed hydrogel scaffolds are soaked in deionized water (Milli-Q, Millipore) for 3 days prior to cell culture to leach out glycerol and any unpolymerized acrylamide. Reflected light optical microscopy (IX71; Olympus) is performed prior to cell plating to ensure structural integrity of the scaffolds. SEM micrographs are obtained with a Philips XL30 ESEM-FEG; structures are dried and sputter-coated with gold prior to imaging.

3T3 Fibroblast Seeding and Imaging:

The interaction of murine NIH/3T3 fibroblast cells with the printed hydrogel scaffolds are investigated to assess their cytocompatibility. The initial cell stock (density of ~$1\times10^6$ cells/ml) is divided between three T-75 cell culture flasks, to which 20 ml of cell media (Dulbecco's Modified Eagle Medium, DMEM) that consists of 4.5 g/L glucose, 4 mM glucose, 1 mM sodium pyruvate, 1.5 g/L sodium bicarbonate and supplemented with 10% fetal bovine serum (FBS, Colorado Serum Company) and 100 U/ml penicillin/100 µg/ml streptomycin (Sigma Aldrich) is added. The media is exchanged the next day to remove excess dimethyl sulfoxide (DMSO, Sigma Aldrich). Cells are grown in a humidified incubator at 37° C. with 5% $CO_2$.

Hydrogel scaffolds are sterilized prior to cell plating, through UV light exposure in the laminar flow hood for 20 min. Scaffolds are immersed in 100 µg/ml poly-d-lysine (Sigma Aldrich) for 60 min prior to seeding. Flat glass coverslips are also evaluated as controls. Cells are plated onto the scaffolds at approximately $0.5\times10^6$ cells/ml and allowed to proliferate for approximately 48 h. After 2 days in culture, the fibroblasts are rinsed 3 times with PBS, immersed in 4% paraformaldehyde at room temperature for 10 min and then rinsed again with PBS. A PBS solution containing 0.25% Triton X-100 is placed on the cells for 3 min to permeate their membranes and then the samples are rinsed again with PBS. The cells are then incubated in 1% bovine serum albumin (BSA, Sigma Aldrich) in PBS for 10 min. The cells are then incubated for an additional 20 min in a rhodamine-phalloidin (Invitrogen Molecular Probes) solution diluted 1:200 in 1% BSA solution, and again rinsed with PBS. Finally, the samples are incubated with 0.002% DAPI in PBS (4',6-diamidino-2-phenylindole, Invitrogen Molecular Probes) for 1 min and rinsed with deionized water. The rhodamine-phalloidin stains actin filaments red, while the DAPI stains the DNA in the nucleus blue. All fluorescent microscopy is performed using the Zeiss Axiovert 200M inverted microscope. A Dapi/Hoechts/AMCA filter (Chroma Technology) is used for the DAPI imaging, a Special Yellow Rhodamine/Cy3/Texas Red filter (Chroma Technology) is used for the rhodamine imaging and the Piston GFP filter is used for imaging the autofluorescence in the hydrogel scaffold.

Poly(2-Hydroxyethyl Methacrylate) (pHEMA) Based Ink Systems

Poly(2-hydroxyethyl methacrylate) (pHEMA) scaffolds with varying 3D microperiodic architecture are created by direct-write assembly, and then rendered growth compliant for primary rat hippocampal neurons by absorption of polylysine. Neuronal cells thrive on these 3D scaffolds, forming differentiated, intricately branched networks. Confocal laser scanning microscopy reveals that both cell distribution and extent of neuronal process alignment depend upon scaffold architecture.

Mammalian tissues are composed of intricate matrices of individual cells that receive complex cues from their three-dimensional (3D) environment. Yet standard cell culture methods rely on two-dimensional (2D) substrates that are poor mimics of real tissue environments. This deficiency is especially relevant to brain tissue, where neurons exchange critical information across synapses and the 3D organization of neurons and their supporting cells is critical for function. It is well known that neuronal cells, among others, are strongly influenced by their surrounding microenvironment; for example, process orientation is guided by both topographical and chemical cues. Most prior studies of neuronal cell cultures have focused on planar or semi-planar environments, even though emerging evidence suggests that many cell types display important biological differences in 3D systems. Hence, new biocompatible scaffolds with precisely controlled features and interconnected porous networks are desired to understand how 3D environments affect the integration and behavior of neuronal cells and other cell types.

Three-dimensional scaffolds of varying microperiodicity are created using a pHEMA-based ink that contains high molecular weight pHEMA chains dissolved in a photocurable HEMA monomer solution. In this ink design, the pHEMA chains serve as a viscosifying agent to allow the printed features to retain their filamentary shape and span gaps in the underlying layer(s). After printing, the 3D hydrogel scaffolds are photocured to enhance their mechanical integrity ensuring survival upon immersion in aqueous culture solution.

pHEMA Ink Preparation:

Poly(2-hydroxyethyl methacrylate) (pHEMA), Mw=300,000 and 1,000,000), hydroxyethyl methacrylate (HEMA), ethylene glycol dimethacrylate (EGDMA), and 2,2-dimethoxy-2-phenylacetophenone (DMPA) are obtained from Sigma-Aldrich (St. Louis, Mo.). pHEMA inks are prepared by first combining the following constituents: deionized water, HEMA monomer, and the crosslinker, EGDMA. The photoinititor, DMPA, is then added to this solution and stirred until dissolved. Finally, pHEMA is added and the mixture is stirred for 24-72 h until the pHEMA completely dissolves and forms a homogenous solution. The pHEMA inks are stored in a dark location to prevent premature crosslinking. An optimal ink formulation is 25 wt % pHEMA (300,000 Mw), 10 wt % pHEMA (1,000,000 Mw), 40 wt % HEMA, 23.5 wt % H2O, 1 wt % EGDMA, and 0.5 wt % DMPA.

Scaffold Fabrication:

Glass substrates (12 mm diameter, 0.17 mm thickness, Warner Instruments) are piranha cleaned and soaked in a 5% 3-(Trimethoxysilyl)propyl methacrylate (Sigma) in toluene solution at 60° C. overnight and rinsed with isopropanol. 3D pHEMA scaffolds are fabricated using a 3-axis micropositioning stage (ABL9000, Aerotech Inc.) controlled by customized software (3D Inks). The ink is housed in a syringe (3 ml, EFD Inc.) mounted on the stage and extruded through a tapered micronozzle (10 µm, World Precision Instruments) onto the prepared substrates under an applied pressure of 100-200 kPa (800 Ultra dispensing system, EFD Inc.) at a speed of 200 µm $s^{-1}$. After patterning the initial layer, the nozzle is incrementally raised in the z-direction to generate the next layer, and repeated until the desired 3D scaffold architecture is formed.

After printing, each scaffold is exposed to UV light (Omni-Cure S2000, Exfo) for ~20 min and soaked in deionized water for at least 12 h to remove any unreacted species. The scaffolds are printed with 6 layers with overall dimensions ranging from $1\times1$ mm$^2$ to $1.16\times1.16$ mm$^2$. The center-to-center separation distance (or pitch) between pHEMA filaments ranges from 30-80 µm. SEM images of 3D unseeded pHEMA scaffolds are taken with a Hitachi S-4700 SEM after coating samples with gold/palladium for 45 s (Emitech K575 Sputter Coater).

Figures 5A, 5B, 5C, 5D:
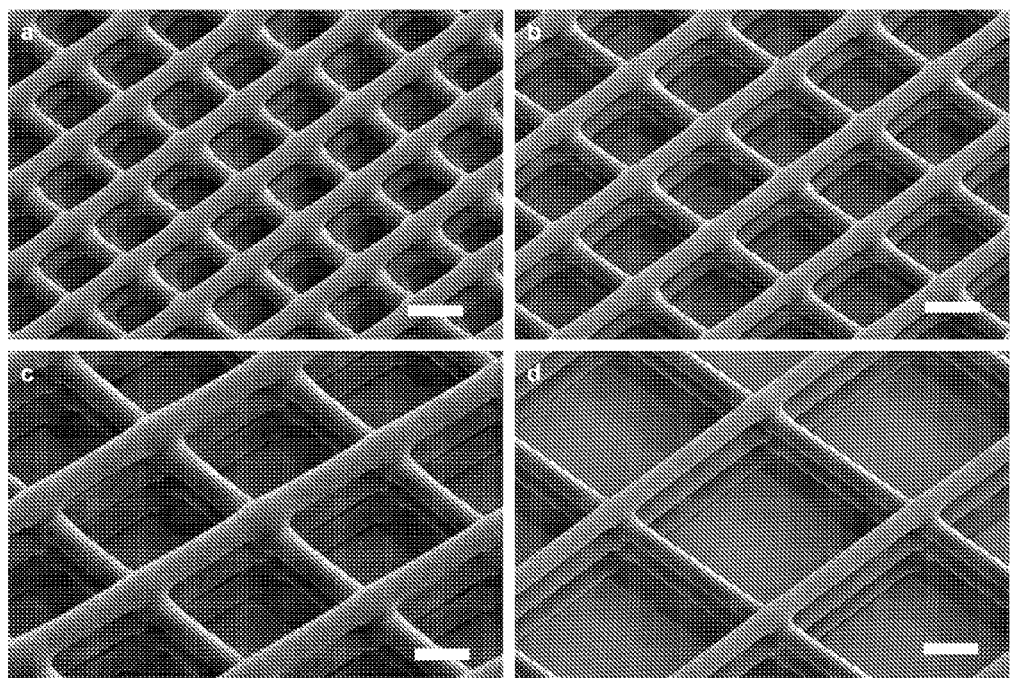
FIGS. 5(a)-5(d) are SEM micrographs of 3D poly(2-hydroxyethyl methacrylate) (pHEMA) scaffolds of varying architecture that possess a center-to-center separation distance between patterned filaments of (a) 30 μm, (b) 40 μm, (c) 60 μm, and (d) 80 μm, where all scale bars are 20 μm.
Figures 10A, 10B, 10C:
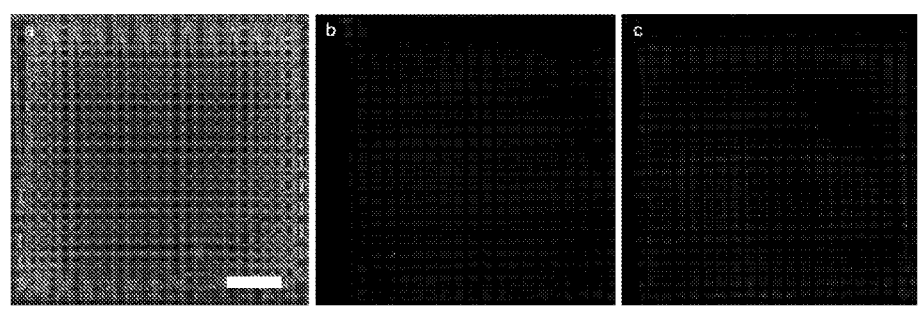
FIGS. 10(a)-10(c) show fluorescent micrographs of the 3D pHEMA scaffolds after exposure to (a) FITC-polylysine, (b) FITC-Protein A and (c) FITC-IgG, indicating that only polylysine is strongly absorbed by these structures (scale bar, 200 μm)
Figures 11A, 11B, 11C, 11D:
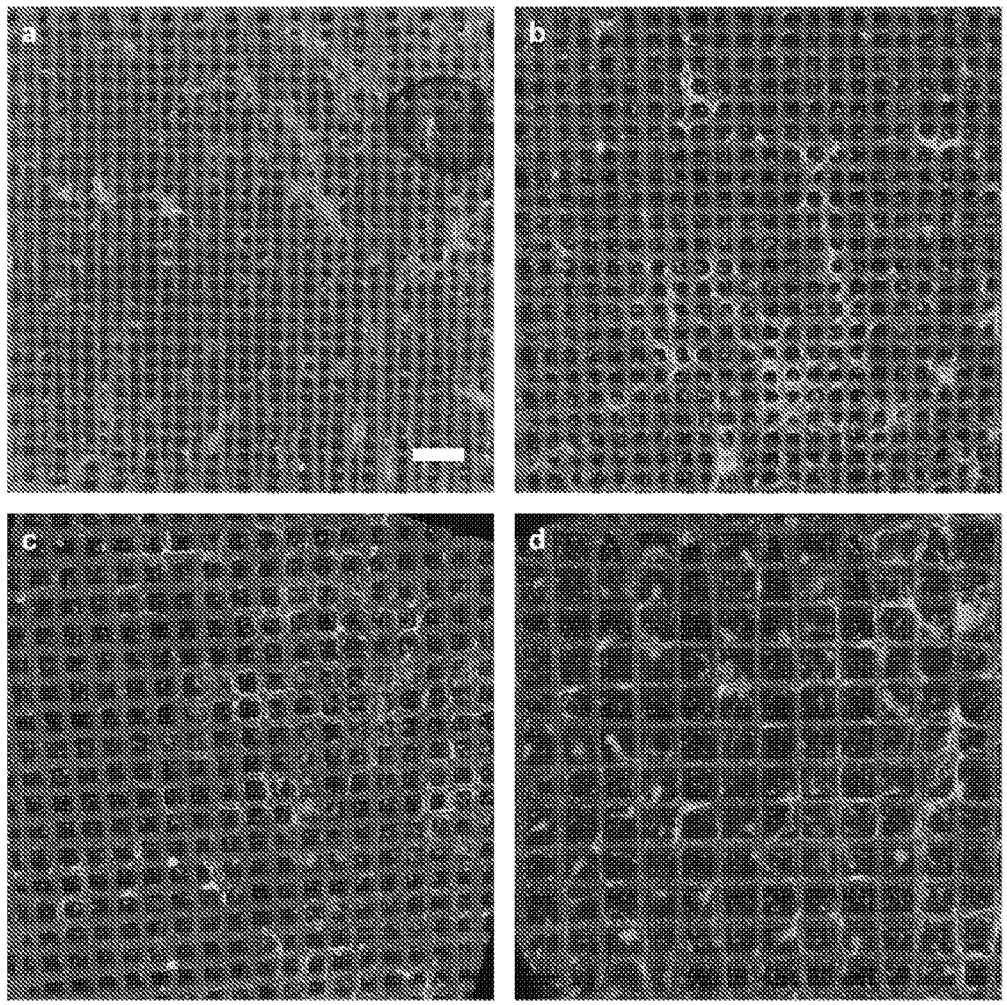
FIGS. 11(a)-11(d) show low magnification (tiled) confocal images of primary rat hippocampal cells interacting with 3D pHEMA scaffolds of varying pitch: (a) 30 μm, (b) 40 μm, (c) 60 μm, and (d) 80 μm, which highlight significant neuronal integration throughout each scaffold. In these images, actin in the cytoskeleton is stained green, while the cell nuclei are stained red (scale bar, 100 μm)

Four scaffold architectures are produced, each of which contains orthogonal arrays of cylindrical hydrogel rods (ca. 10 µm in diameter) with a varying center-to-center spacing between adjacent rods of 30, 40, 60, and 80 µm (see FIGS. 5(*a*)-5(*d*)). Prior to cell culture, scaffolds were sterilized for 20 minutes in a laminar flow hood. To render the scaffolds growth compliant for primary rat hippocampal neurons, they are chemically modified by immersion in a polylysine solution, where rapid absorption of these polypeptide species occurs (see FIGS. 10(*a*)-10(*c*)).

Figures 12A, 12B:
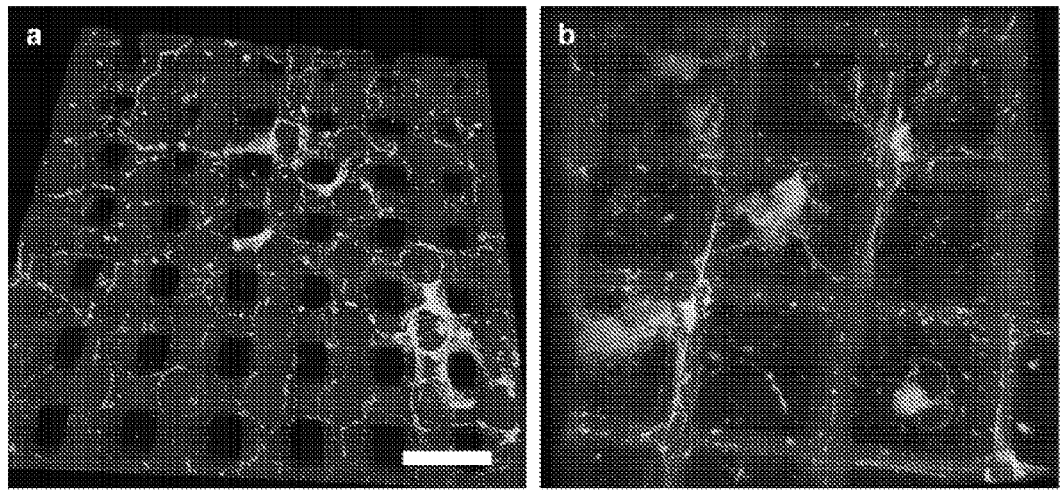
FIGS. 12(a)-12(b) are reconstructed tiled, confocal images that highlight staining for the neuronal marker MAP2 (shown in green) for 3D pHEMA scaffolds with (a) 40 μm and (b) 80 μm pitch (scale bar, 40 μm)

Cell Culture Results:

After sterilization and subsequent treatment with unlabeled polylysine, the 3D hydrogel scaffolds are plated with post-natal day 1 primary rat hippocampal neurons. After seven days in vitro, the cultured neurons form extensive differentiated networks within the 3D scaffolds, as shown in the reconstructed CLSM images in FIGS. 6(a)-6(d) and in lower magnification images provided in FIGS. 11(a)-11(d). The cells are integrated throughout each scaffold, with neuron response being dependent upon the scaffold architecture. As the spacing between adjacent patterned rods increases, there is a decrease in the number of cell somata that are fully integrated throughout the 3D scaffold and an increase in the number of neuronal networks established on the underlying glass substrate. The cell survival in each scaffold is high and the cultures develop stably without evidence of cell division. At seven days in vitro, cells show elaborate processes that exhibit MAP2, a protein commonly present in dendrites. (see FIGS. 12(a)-12(b))

FIGS. 6(a)-6(d) show a top view of each 3D scaffold that highlights neuronal process organization, as well as a reconstructed side view, which illustrate cell distribution along the vertical direction. For scaffolds with a pitch of 30 μm, the majority of cell somata and their respective processes are confined to the top layers of the scaffold (FIG. 6(a)). The neuronal processes clearly follow along the scaffold rods, which is expected given that hippocampal neurons preferentially attach to and follow along planar surface topographies, such as those formed by patterned post arrays. As the scaffold pitch increases to 40 μm, the neurons create highly branched and aligned networks where the cell bodies are well distributed within the vertical dimension (FIG. 6(b)). On this scaffold, the neuronal processes are able to penetrate all layers, instead of being confined to those near the top. When the scaffold pitch is further increased to 60 μm, the open pore channels are large enough to facilitate the partitioning of cells to lower layers, where they attach to the underlying substrate (FIG. 6(c)). On these scaffolds, however, three-dimensionally supported neuronal networks do develop. As the pitch is increased further to 80 μm, the dominant somata response is the formation of intricate neuronal networks on the underlying substrate surface (FIG. 6(d)). Typically, these networks consisted of 1-2 neurons in each compartmentalized "pore" space with cellular processes that interact and densely follow the contours of the overlaying scaffold rods.

Figures 7A, 7B:
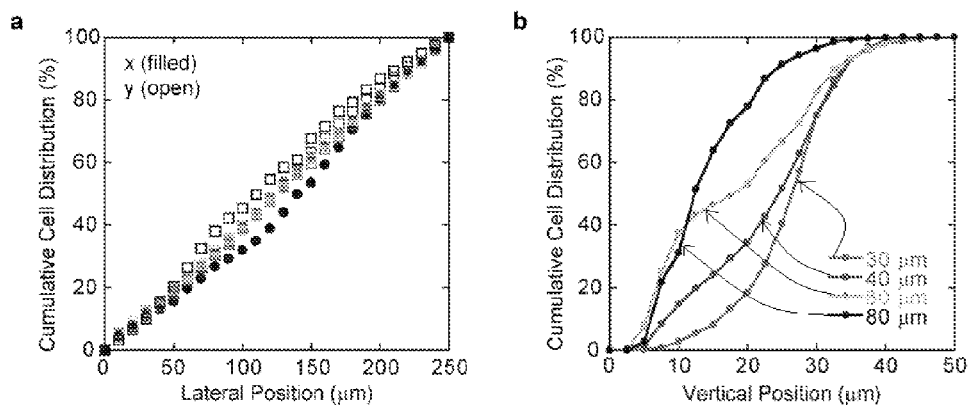
FIGS. 7(a)-7(b) show neuron cell distribution as a function of (a) lateral and (b) vertical position within 3D pHEMA scaffolds of varying architecture.

The cell soma distribution is quantitatively assessed as a function of lateral and vertical position (FIGS. 7(a)-7(b)) by 3D image analysis of confocal scans acquired in a representative volume of 250×250×~50 μm$^3$ within each scaffold. While the cells are well distributed laterally (FIG. 7(a)), the pitch between filaments determines their vertical distribution in these scaffolds (FIG. 7(b)). At the smallest pitch of 30 μm, the distribution is somewhat skewed to the upper layers of the scaffold (FIG. 7(b)). In this architecture, the characteristic pore size is ~20-22 μm, which may hinder the ~10 μm somata from efficiently integrating deep within the scaffold. In scaffolds with a 40 μm pitch (~30-32 μm pores), the cell soma are well integrated vertically, while they tended to segregate to the region near the substrate in scaffolds with a pitch of either 60 or 80 μm.

Figures 8A, 8B, 8C, 8D:
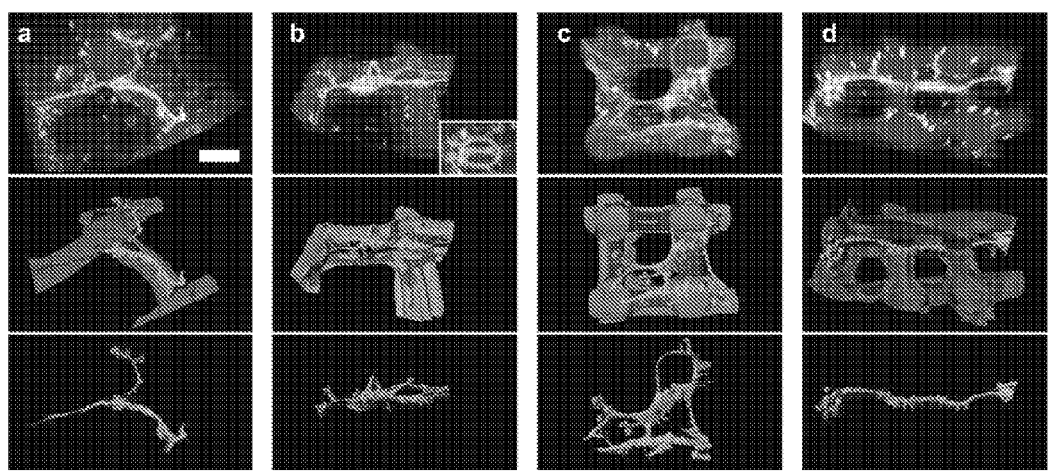
FIGS. 8(a)-8(d) show confocal images of representative neuron cells on the 3D pHEMA scaffolds (top row), reconstructed views (middle row) and reconstructed view of cells only (bottom row) including (a) pyramidal soma morphology on scaffold (60 μm pitch), (b) neuronal process wrapping around cylindrical feature within scaffold (60 μm pitch), (c) soma supported by neuronal processes on scaffold (40 μm pitch), (d) process contact guidance on a scaffold (30 μm pitch) (scale bar, 20 μm)
Figure 13:
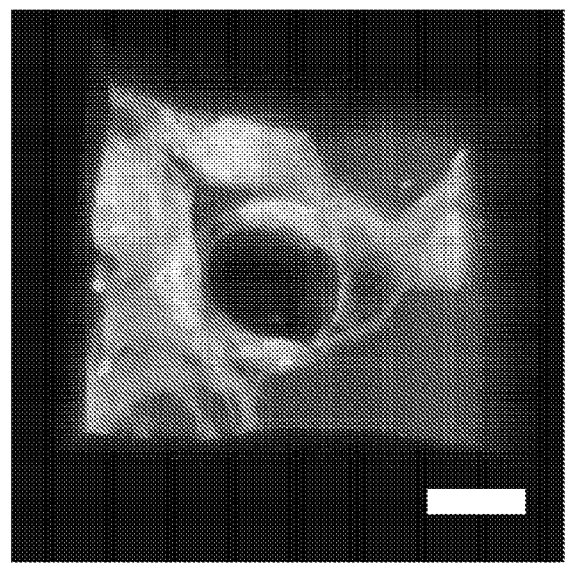
FIG. 13 is a reconstructed confocal image of neurons in 3D scaffold of 30 μm pitch, which highlights the tendency for neuronal somata (marked by nuclei labeled in red) to insert themselves into the interacting regions between scaffold rods (red) (scale bar, 10 μm)

To probe specific cell morphologies and process outgrowth behavior, individual cells are isolated and reconstructed in 3D through image analysis. Confocal images and reconstructions of representative cells are shown in FIG. 8(a)-8(d). In the actual images, the scaffold and cell nuclei are stained red and the processes are green. In the reconstructions, the nuclei are colored blue, the actin in the cytoskeleton is green, and the cell nuclei are colored red. The neuronal soma in FIG. 8(a) displays a pyramidal morphology, which is commonly present in planar in vitro cultures of hippocampal neurons. This 3D reconstruction reveals that the neuronal process follows underneath the scaffold on one side, while navigating over the top of the scaffold rod on the other. In FIG. 8(b), a cell body is seen to attach horizontally to the scaffold while its processes wrap around the adjacent rod in a high symmetry that maximizes multi-rod surface contacts. The inset reveals the process wrapping more clearly in a cross-sectional view. This behavior is most commonly observed on the topmost layers of scaffolds with the three smallest pitch sizes, where the neuronal processes can more easily access and interact with the entire circumference of the printed hydrogel rods. Somata with a distorted cell shape are also observed as they fit themselves between scaffold layers (see FIG. 13), highlighting a strong preference for interaction with the scaffold surface.

While it appears that the majority of cell bodies prefer to interact with these 3D scaffolds, some somata are vertically suspended with only their neuronal processes providing the necessary anchorage to the scaffold (FIG. 8(c)). This suggests significant neuronal migration after plating onto the scaffold structures. An interesting morphology is revealed in this image where, instead of wrapping around an individual hydrogel rod, the process wraps around junctions formed at orthogonal intersections between printed rods in adjacent layers (a behavior most typically observed on scaffolds of the two smallest pitch sizes). Broader contact guidance along the two perpendicular scaffold orientations is observed on all scaffold architectures. An example of this is given in FIG. 8(d), where the neuronal processes of a soma in a 30 μm pitch scaffold are clearly guided by the patterned features.

Figures 6A, 6B, 6C, 6D:
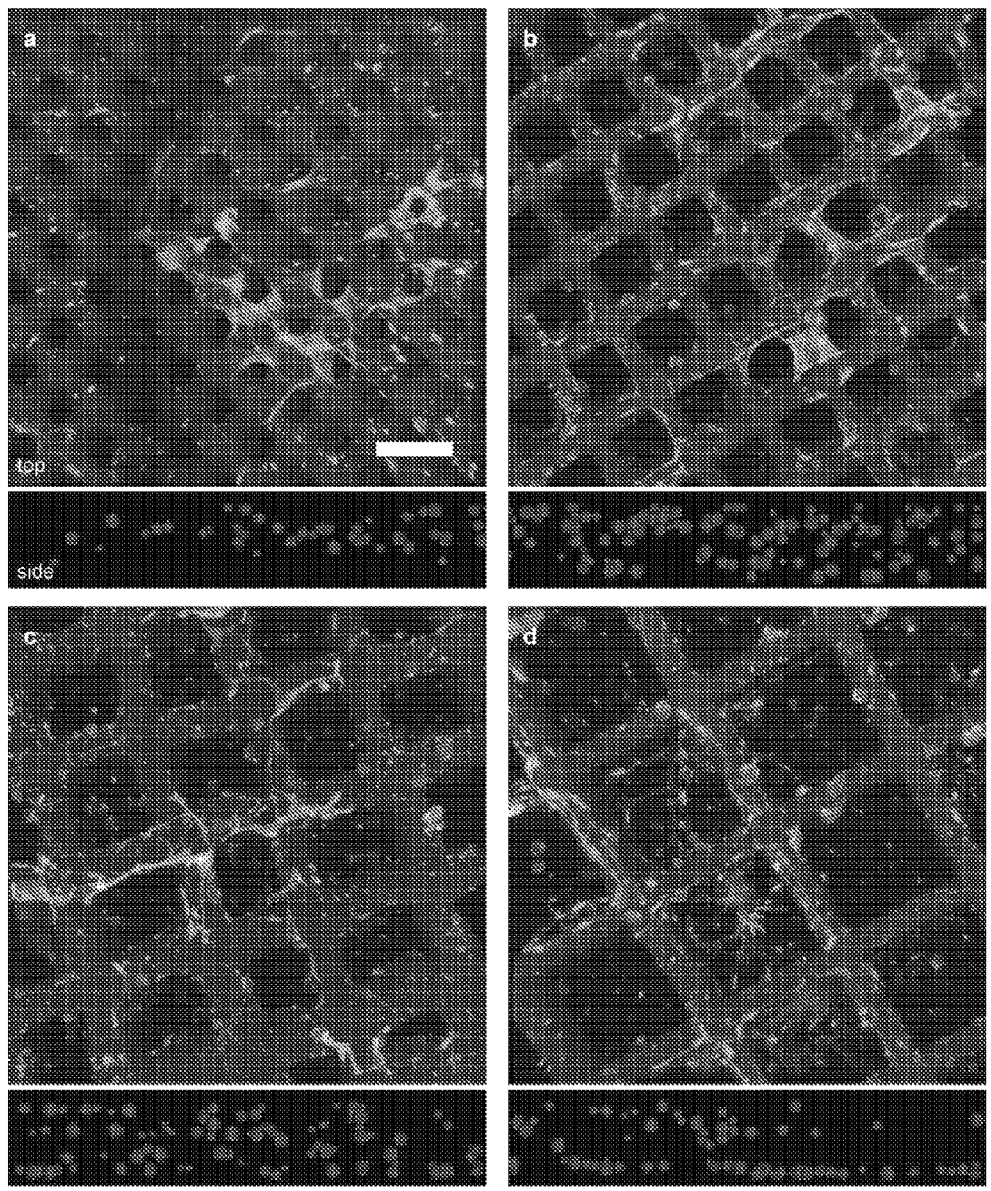
FIGS. 6(a)-6(c) are confocal images (x-y scans, tiled) of primary rat hippocampal neuron cells distributed within 3D pHEMA scaffolds of varying pitch: (a) 30 μm, (b) 40 μm, (c) 60 μm, and (d) 80 μm, where a primary monoclonal antibody for actin is used to label the processes, and TO-PRO3 is used to label nuclei; side view reconstructions denote the positions (in x-z plane) of the neuronal somata, while their relative size indicates their position along the y-axis (scale bar, 40 μm)
Figures 9A, 9B, 9C, 9D, 9E, 9F:
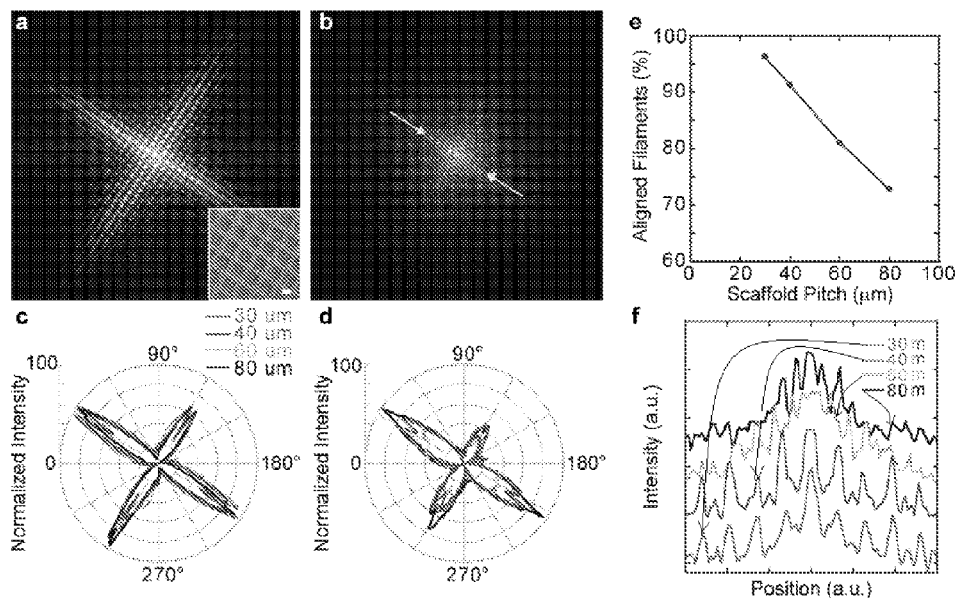
FIGS. 9(a)-9(b) show planar representations of 3D fast Fourier transform (FFT) calculated for (a) 3D pHEMA scaffold with 40 μm pitch and (b) corresponding neuronal processes on this scaffold, where the inset in (a) is an SEM image that indicates scaffold orientation.
FIGS. 9(c)-9(d) show normalized intensity as a function of angle for (c) scaffolds of varying pitch and (d) neuronal processes calculated from the FFTs.
FIG. 9(e) shows the extent of cellular process alignment as a function of scaffold pitch.
FIG. 9(f) shows line scans of intensity measured across the primary angle of the neuronal process alignment in the FFTs (denoted by arrows in FIG. 9(b)) (scale bar, 20 μm)

To quantify the neuronal process alignment, separate fast Fourier transforms (FFT) are calculated for both the scaffolds and neuronal processes observed in the 3D reconstructed images. FFTs acquired from a 3D scaffold (40 μm pitch) and corresponding neuronal processes, shown in FIGS. 9(a)-9(b), reveal the strong periodicity of both the scaffold and the interacting neuronal processes. The inset in FIG. 9(a) denotes the scaffold orientation. These images are analyzed and plotted for the specific rod and process fluorescence intensities as a function of angle (FIGS. 9(c)-9(d)). The similarities between the two polar plots indicate that the neuronal processes have a similar degree of periodicity as the scaffolds, signifying that the processes closely follow along the topography of the scaffold. The anisotropy of this process alignment on the scaffolds can be approximated from the 3D reconstructions, as shown in FIG. 9(e). As expected, the correlation length of this induced anisotropy decreases as the pitch size increases. The intensity line scans taken across the primary angle in the neuronal process FFTs, shown in FIG. 9(f), indicates that the processes exhibit a higher degree of periodicity within 3D scaffolds of smaller pitch (i.e., 30-40 μm). Interestingly, scaffolds with 40 μm pitch present a better peak-to-noise ratio than those of 30 μm pitch. This may be due to the increased proclivity for processes to form bridges that span between rods in scaffolds of finer pitch, as illustrated in FIG. 6(a).

In summary, 3D microperiodic hydrogel scaffolds offer a robust, biocompatible culture system for primary hippocampal neurons. Using confocal microscopy coupled with image analysis, cell-scaffold interactions were observed and quantified in 3D allowing further insight to neuronal development in complex environments. This programmable 3D platform offers new opportunities for studying and controlling the distribution of hippocampal neurons in three dimensions, which may be extended to other sensitive cell types and tissues.

Figures 14A, 14B, 14C, 14D:
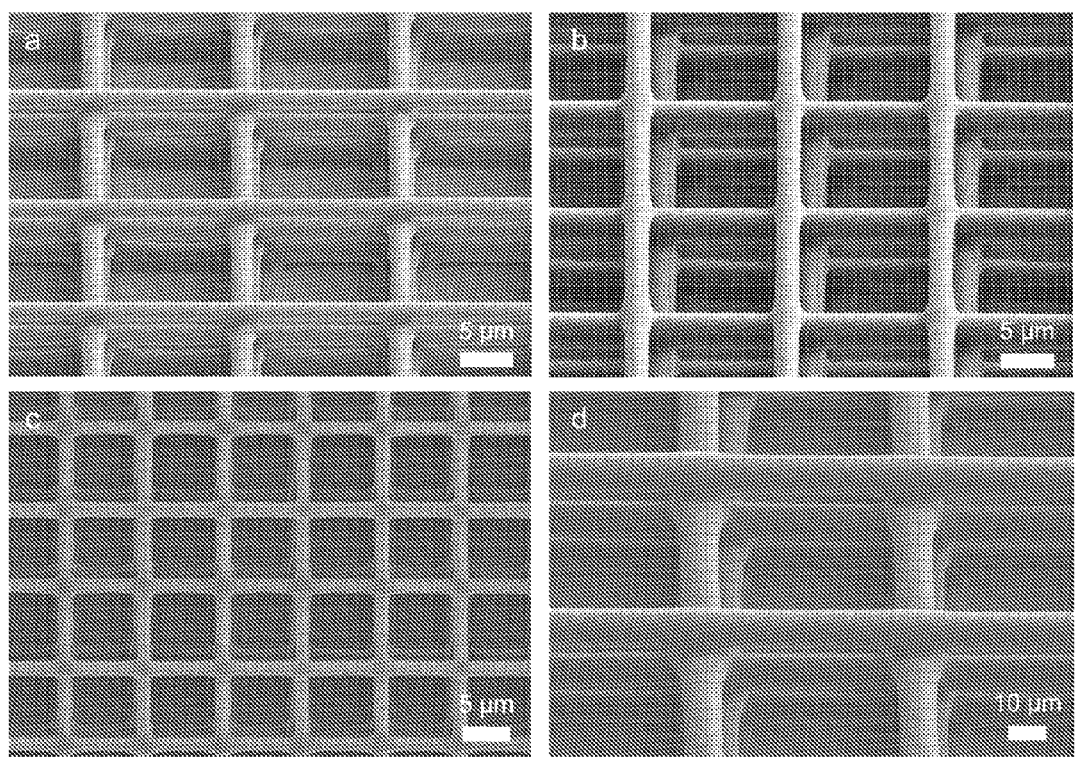
FIGS. 14(a)-14(d) show hydrogel scaffolds formed from 35 wt. % pHEMA with a 5:2 ratio of 300 k and 1M g/mol polymers.

Ink Rheology:

To achieve greater control over the rheological properties, a bimodal molecular weight distribution of pHEMA may be used to form the ink. By blending two different molecular weights (300 k and 1M g/mol) of pHEMA, optimal rheological behavior can be obtained. The SEM images of FIGS. 14(a)-14(d) demonstrate the process flexibility of the hydrogel ink composed of 35 wt % pHEMA with a 5:2 ratio of 300 k and 1M g/mol polymers. The pHEMA ink can be printed through nozzles ranging from 1 to 10 µm into filaments without deformation. The vertical spacing can also be increased by printing adjacent layers aligned in the same direction, as demonstrated for the double layered scaffold in FIG. 14(b).

Figures 15A, 15B:
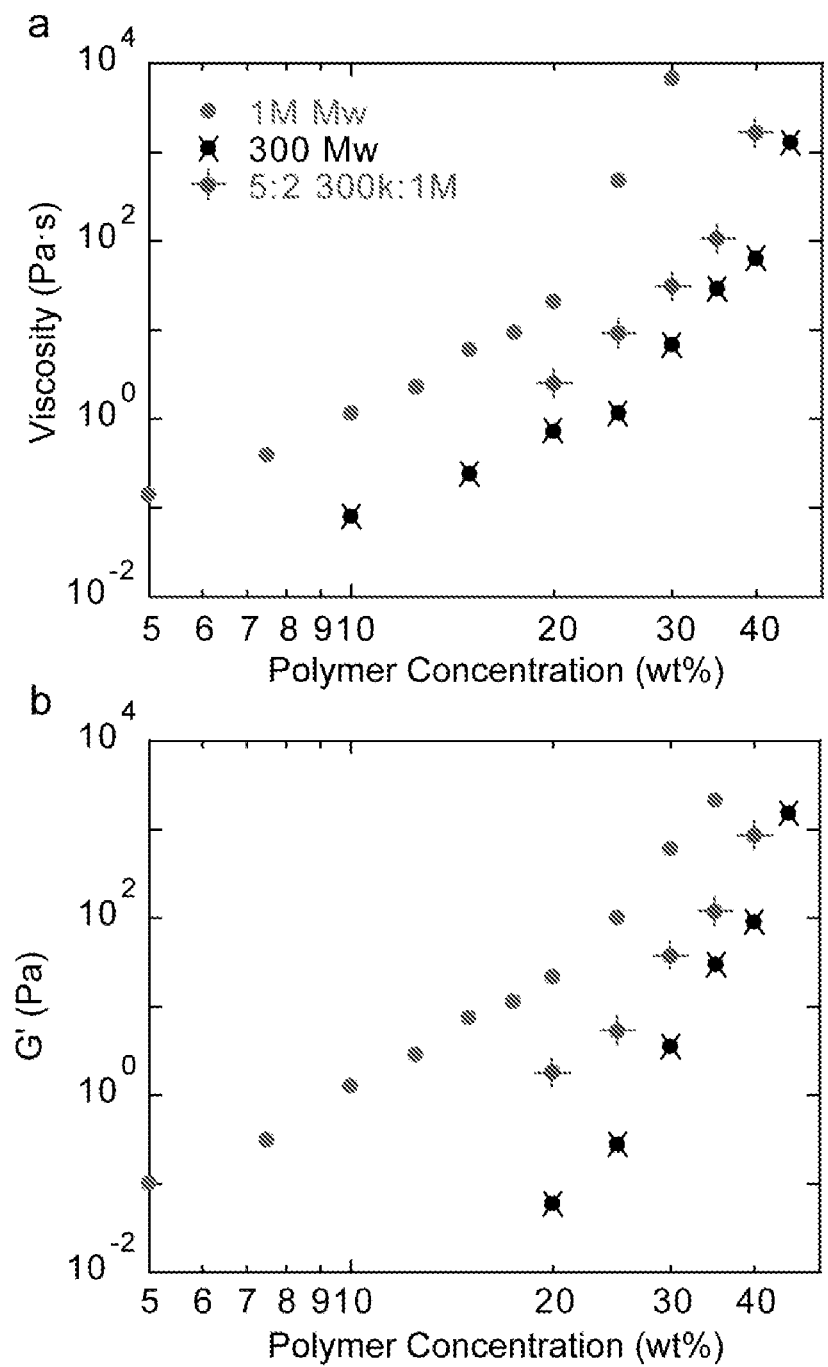
FIGS. 15(a)-15(b) show shear viscosity and elastic modulus (G') as a function of polymer concentration for 300,000 and 1,000,000 MW pHEMA solutions and the pHEMA ink of FIGS. 14(a)-14(d)

FIGS. 15(a)-15(b) illustrate the low shear viscosity and elastic modulus (G') as a function of polymer concentration for 300 k and 1M g/mol pHEMA solutions and pHEMA-based inks comprised of a 5:2 300 k:1M polymer ratio blend. Although the curves look similar, the 1 g/mol pHEMA contributes significantly to increasing the viscosity of the solution. For example, there are three compositions that have a similar G L 100 Pa: 25 wt % 1M g/mol, 35 wt % 5:2 300 k:1M weight ratio blend, and 40 wt % 300 k g/mol pHEMA. However, the viscosities for these solutions are 480 Pa·s, 110 Pa·s, and 60 Pa·s, respectively.

Figure 16A:
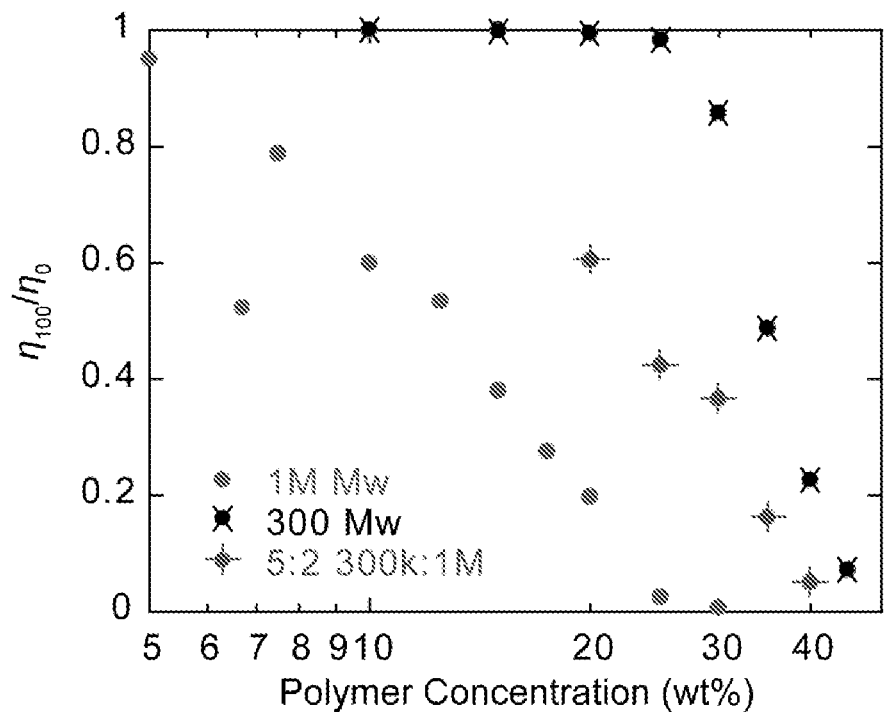
FIGS. 16(a)-16(b) show (a) ratio of high shear viscosity (100 1/s) to low shear viscosity as a function of polymer concentration and (b) shear thinning behavior for the same pHEMA ink.
Figure 16B:
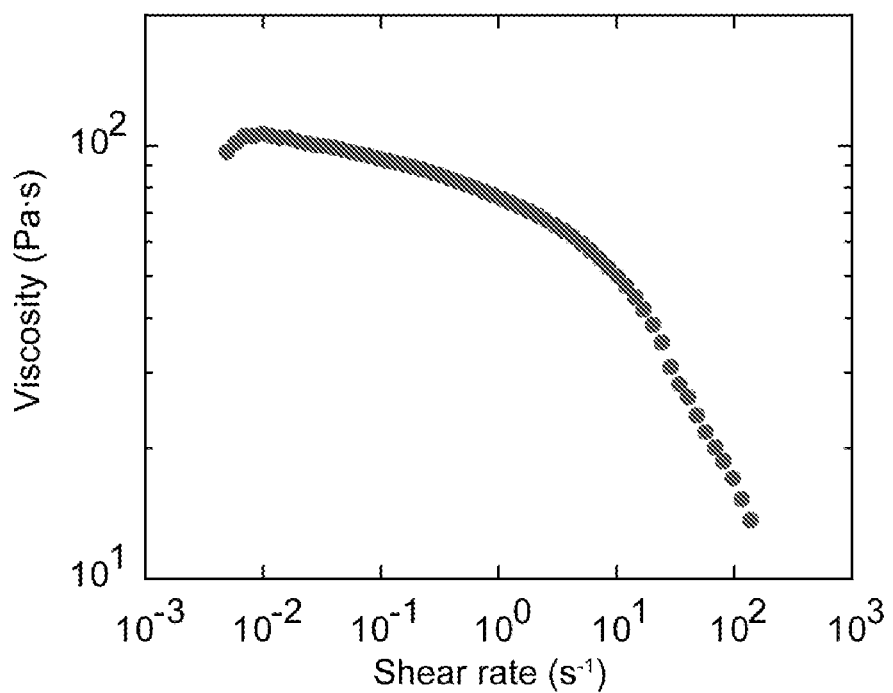

The high molecular weight chains impart important properties to the ink. The longer chains align under shear, decreasing the viscosity as the shear rate increases. The ratio of the high shear viscosity (100 1/s) to the low shear viscosity is presented as a function of polymer concentration. FIG. 16(b) shows an example of the shear thinning behavior for the 35 wt. % 5:2 300 k:1M weight ratio blend pHEMA ink. The polymer blends shear thin significantly, even at low concentrations, caused primarily by the higher molecular weight component. This behavior improves printability, as the ink must be able to easily flow out of the micronozzle under an applied shear. Additionally, the long chain polymers aid in forming a continuous filament during the printing process.

Figures 17A, 17B:
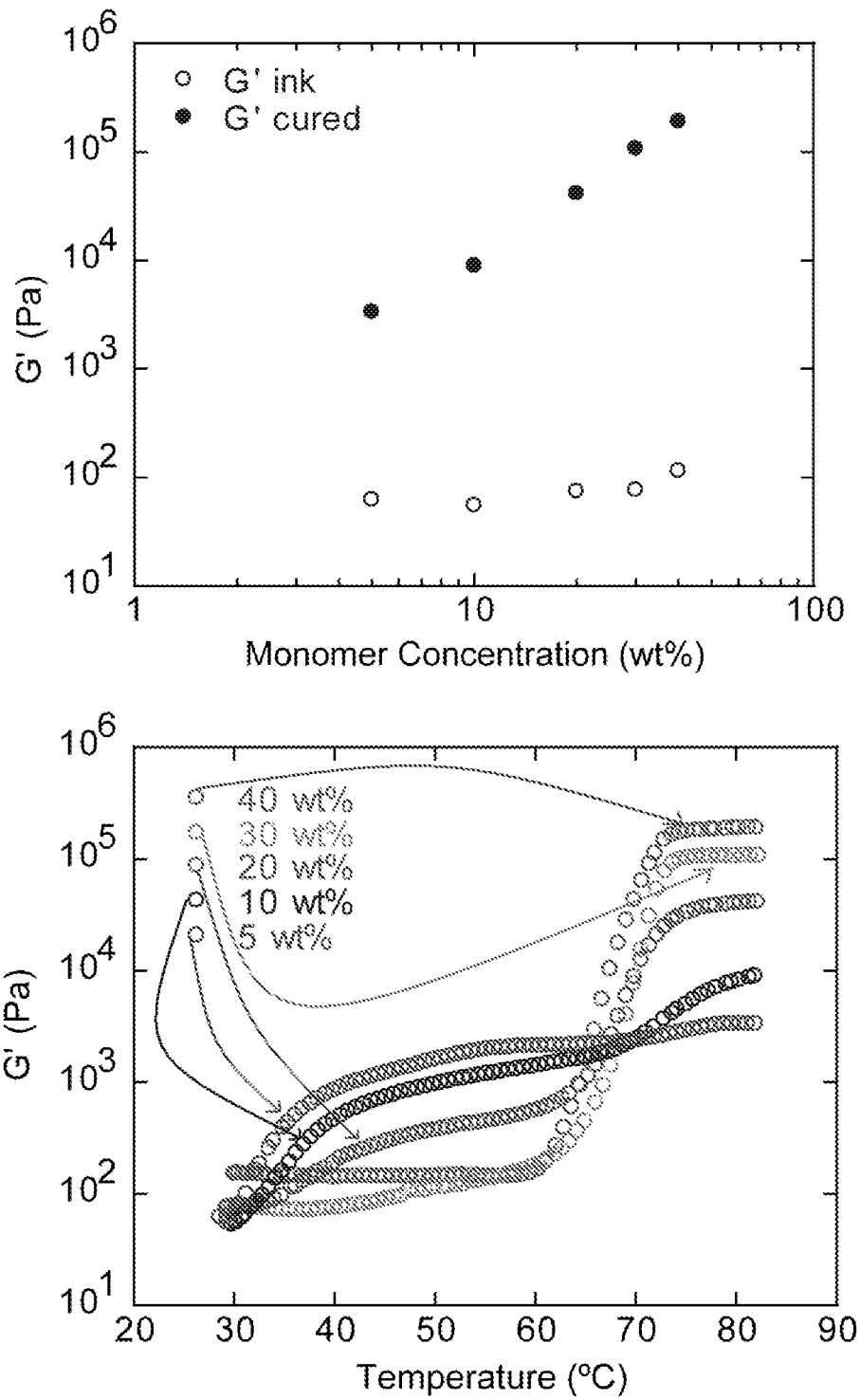
FIGS. 17(a)-17(b) show the pHEMA ink elasticity as a function of (a) monomer concentration and (b) temperature.

Instead of a photoinitiator, a thermal initiator can be used to probe the rheological properties during the curing of the ink as a function of temperature. In FIG. 17(a), the amount of monomer concentration of the ink is varied while maintaining the polymer concentration at 35 wt. % and the crosslinker concentration at 1 wt. %. Changing the monomer concentration has little effect on the rheological properties of the ink, but the corresponding cured hydrogels have elasticity values that are increased by over two orders of magnitude, from 3 to 190 kPa (FIG. 17(b)). Some drying does occur in the rheometer from EtOH, which is used to help dissolve the polymers when the monomer concentration<30%.

Figures 18A, 18B:
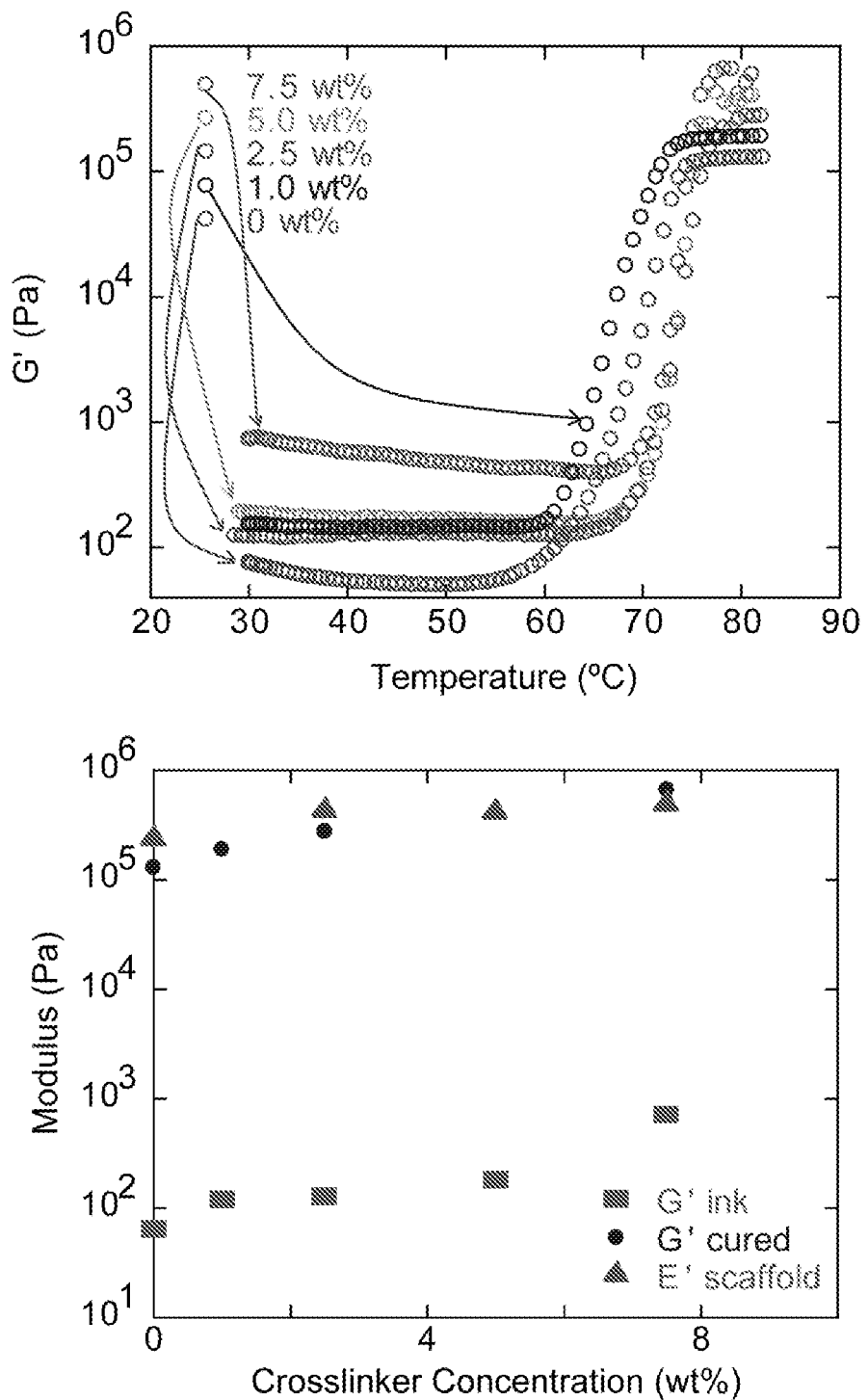
FIGS. 18(a)-18(b) show the influence of crosslinker concentration on the cured pHEMA's elastic properties.

Referring to FIGS. 18(a)-18(b), the amount of crosslinker can also affect the cured hydrogel's elastic properties. Varying the amount of the crosslinker, EGDMA, from 0 to 7.5 wt % gives a range of G' from 130 to 670 kPa. E' has also been measured using AFM nanoindentation on printed scaffolds and similar values were found.

Additional Experimental Details

Hippocampal Neuron Culture:

Prior to use in culture, pHEMA scaffold samples were sterilized for 20 min with UV, treated with poly-D-lysine (MW: 30-70 kDa, Sigma) at 100 µg/ml for 1 h, and then allowed to sit for 1 h.

Hippocampal neurons are isolated from post-natal day one (P1) Long Evans/BluGill rats (University of Illinois-Urbana Champaign). The brains are removed, the hemispheres separated, and the hippocampi dissected. Dissected tissue is kept in a 35 mm petri dish, surrounded by ice and filled with cold Hibernate A base solution (Brain-Bits), supplemented with 2% B-27 (Invitrogen) and L-glutamine (0.5 mM, Sigma). Upon completion of dissection, the tissue is incubated with Papain enzyme (2 mg/ml, Worthington) at 37° C. for 15 min and then rinsed with 2 ml Hibernate A solution. The solution is removed, an additional 2 ml of Hibernate is added, and then the tissue is triturated approximately 10 times. After allowing the large pieces of tissue to settle, the cell solution is collected. This step is repeated at least once. The cell solution is centrifuged for 5 min at 3G and then reconstituted with 0.5 ml of Neurobasal base solution (Gibco), supplemented with 2% B-27 (Invitrogen), L-glutamine (0.5 mM), and 1% pen-strep (Sigma). The remaining large chunks of tissue are incubated again with papain enzyme (2 mg/ml) for 15 min and the above process is repeated. Once the incubation time is complete, the cell suspensions are combined and used to plate the scaffold substrates at an initial density of approximately 500 cells/mm$^2$. The neurons are maintained in a humidified environment at 37° C. with 5% $CO_2$ and supplemented with Neurobasal media twice weekly for one week.

Confocal Imaging:

Confocal images are acquired using a Zeiss LSM 710 multi-photon confocal microscope. Tiled images of the entire scaffold are obtained using the 25× objective, which are composed of either 3×3 tiles (927 µm×927 µm) or 4×4 tiles (1270 µm×1270 µm) depending on the scaffold architecture. In addition, 2×2 tiled images (250 µm×250 µm) are captured using a 40× objective for data analysis.

Image Analysis:

Confocal z-stacks were reconstructed using Imaris software (Bitplane, Inc.). The distribution of cells was determined using the Spots Analysis. At least two samples, from different culture dates, are analyzed for each scaffold architecture. Position data is imported into MATLAB (The MathWorks) and viewed in 3D from the x-z plane, in which cell size is varied to indicate its position along the y-axis.

Scaffold and neuronal process z-stacks are reconstructed into separate 3D arrays using MATLAB. A Multidimensional Fast Fourier Transform (FFT) package is used to analyze the 3D arrays. The function 'fftn' is used to determine the 3D FFT; 'fftshift' is then used to center the low frequency components of the transform. The power spectrum is taken as the log of the absolute value of the centered transform and scaled identically between samples to display in the grayscale color range 0 to 255. In order to determine the orientation of the neuronal processes, the 'fanbeam' function is used to integrate around the lateral (x-y) and vertical (x-z) orientations, in which the lateral orientation possesses the highest intensity. Only the center beam of the 'fanbeam' projection is used in a 360° rotation. A low pass filter is used on each FFT image to remove the lowest value, and then the data is normalized. Intensity linescans are taken across the primary angle in the process FFT images using ImageJ (U.S. NIH). Dilated scaffold 3D arrays are subtracted from the process 3D arrays to calculate the percent of the neuronal network on the scaffold.

Immunocytochemistry—Actin/Nucleus Staining:

After 7 days in culture, neurons are rinsed 3 times with PBS, immersed in 4% paraformaldehyde at room temperature for 30 min and then rinsed again with PBS, 2×. A PBS solution containing 0.1% Triton X-100 is placed on the samples for 15 min to permeablize cellular membranes, before rinsing again with PBS (0.1% Tween). The samples are then incubated in ITsignal FX (Invitrogen Molecular Probes) for 30 min and then rinsed briefly with PBS (0.1% Tween). Samples are incubated in a 1:100 solution (with PBS and 100

μl of ITsignal FX) of mouse anti-actin monoclonal antibody (MP Biomedicals, Solon, Ohio) for 2 h and then rinsed with PBS (0.1% Tween), 3× (5 min). Cells are incubated for 1 h with a secondary antibody, Goat Anti-Mouse Alexa 568 (Invitrogen Molecular Probes) in a 1:200 dilution (with PBS and 100 μl of ITsignal FX) in the dark. Samples are rinsed with PBS (0.1% Tween), 3× (5 min) and then exposed to To-Pro3 (Invitrogen Molecular Probes) at 5 μM in PBS, for 30 min in the dark. Once the exposure is complete, the samples are rinsed briefly with PBS (Tween 0.1%) and then mounted in Prolong Gold (Invitrogen). Samples are sealed after 24 h and kept covered, at 4° C. until imaged. Note, samples from 4 different in-vitro experiments are stained using this protocol and analyzed.

Immunocytochemistry—MAP2:

Samples are also stained for the cytoskeletal protein MAP2 in the following manner. After 7 days in vitro, samples are quickly rinsed 3× with warm PBS and then immersed in 4% paraformaldehyde (37° C.) for 30 min. Samples are rinsed 2× with PBS (0.1% Tween) and then exposed to 0.1% Triton X-100 PBS solution for 15 min. After another 2× rinse with PBS (0.1% Tween), the samples are incubated in a 5% goat serum PBS for 30 min. The samples are then exposed to primary MAP2 rabbit polyclonal antibody (Pierce) at a 1:100 dilution overnight at 4° C. and then rinsed 3× (5 min) with PBS (0.1% Tween). All of the following steps are completed in the dark. Samples are then exposed to a secondary goat-anti rabbit Alexa 568 antibody (Invitrogen Molecular Probes) for 1 h before again being rinsed 3× (5 min) in PBS (0.1% Tween). Finally, samples are exposed to TO-PRO3 (Invitrogen Molecular Probes) at 50 μM in PBS for 30 min. Samples are dried, mounted in Prolong Gold (Invitrogen Molecular Probes) and sealed after 24 h.

Protein Partitioning:

3D pHEMA scaffolds with a 40 μm pitch are exposed to 2 mg/ml solutions of FITC-Polylysine (MW: 30-70 kDa), FITC-Protein A, and FITC-IgG for 1 h. All proteins are purchased from Sigma. Samples are rinsed with deionized water and imaged using an Olympus Epifluorescent Microscope, AX-70 with a CCD camera (Optronic MagnaFire).

Poly(Hyaluronic Acid) (pHA) Based Ink Systems

Direct ink writing of poly(hyaluronic acid) (pHA) based ink systems also has been explored for the fabrication of tissue engineering scaffolds. Among the tested compositions are pure pHA and blended pHA-PEGDA systems, as indicated in Table 1 below. Excess water is initially added to aid in polymer dissolution; this excess water may be evaporated off under heating and stirring at a temperature of about 60° C.

Figure 19:
FIG. 19 shows printing of a 10 wt. % 300,000 Mw poly (hyaluronic) (pHA) system in 50% glycerol, 50% PBS with a 30 micron tip at a write speed of 750 microns/second.
Figure 20:
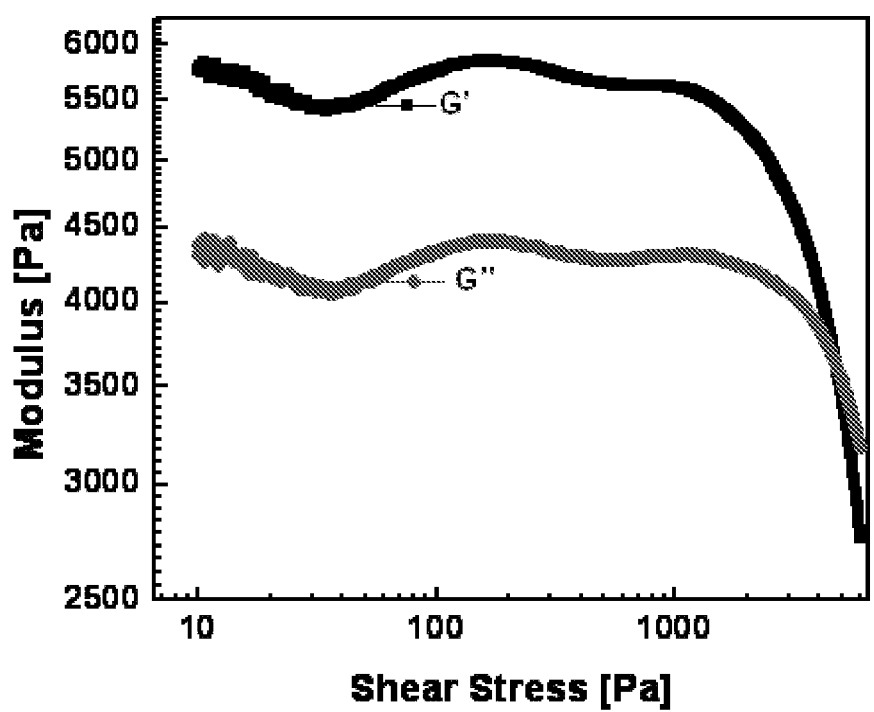
FIG. 20 shows oscillatory rheology for the pHA system of FIG. 19, specifically G' and G" (elastic modulus and viscous modulus, respectively) as a function of shear stress.
Figure 21:
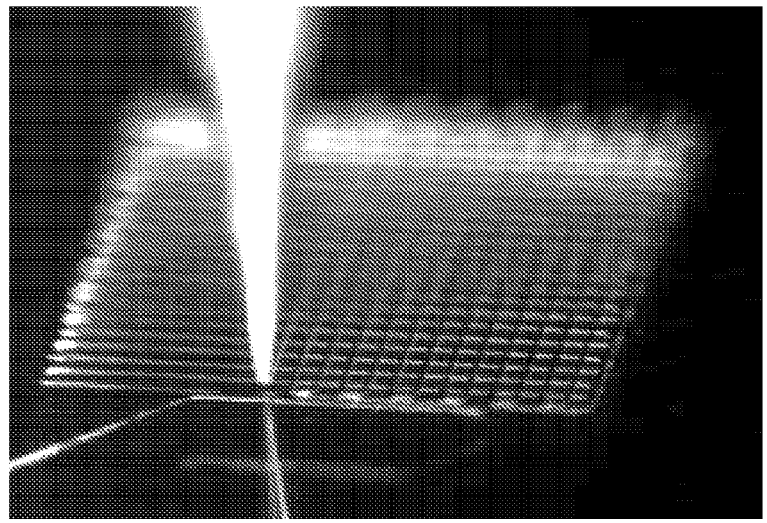
FIG. 21 shows a structure obtained using 10 wt. % pHA, 8 wt. % PEGDA in a 50% glycerol-50% PBS solution, and FIGS. 22 and 23 provide rheological data for the system.
Figure 22:
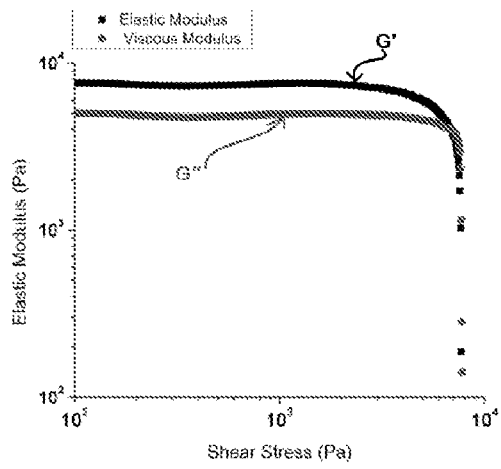
Figure 23:
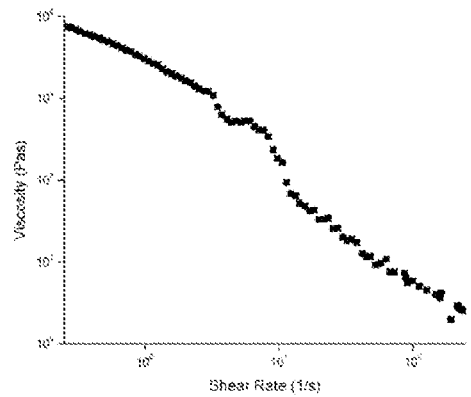

FIG. 19 shows printing of the 10 wt. % 300,000 Mw pHA system in 50% glycerol, 50% PBS with a 30 micron tip at a write speed of 750 microns/second, and FIG. 20 shows the oscillatory rheology for the pHA system, specifically G' and G" (elastic modulus and viscous modulus, respectively) as a function of shear stress. A smooth and well-printed 5-layer thick structure obtained at a write speed of 250 microns/sec and at a pressure of 30 psi using 10 wt. % pHA, 8 wt. % PEGDA in a 50% glycerol-50% PBS solution is shown in FIG. 21, and FIGS. 22 and 23 provide rheological data for the system.

Although the pure pHA system printed well, as indicated by robocasting tests, photocuring the printed scaffolds presented some challenges. It was determined that solubility issues were inhibiting proper photocuring. Irgacure was found to be better suited for the system. In order to improve the mechanical strength of the photocured scaffold, acrylated pHA was employed in addition to a greater concentration of PEGDA. However, there is a tradeoff; at concentrations higher than 10 wt. % PEGDA, the solution becomes oversaturated which may lead to inconsistent printing behavior.

In general, the pure pHA and Blended 1 ink systems are capable of multilayer 2D printing and print well from 100 μm tip dimensions to sub-10 micron tip dimensions. The systems may be cured using 1 minute of UV exposure at an intensity of approximately 100 mW/cm$^2$ for 320 nm light and at an even lower intensity with 250 nm light. The structures can be cured while printing or after printing. Additionally, cured scaffolds have survived in cell media for greater than 2 weeks.

Process parameters for direct ink writing of the Blended 2 system (see Table 1) include the following: pressure of 10 psi, write speed of 100 mm/sec, tip size of 30 μm WPI (painted with nail polish), road width of 130 mm, Z spacing of 15 mm, dimensions of 1500 mm×1500 mm and 2000 mm×2000 mm, cure conditions of 5 W with the Exfo UV lamp for 20 minutes immediately following the completion of the structure, followed by post-curing/drying in the oven overnight (10-12 hours) at 65° C.

Figure 24A:
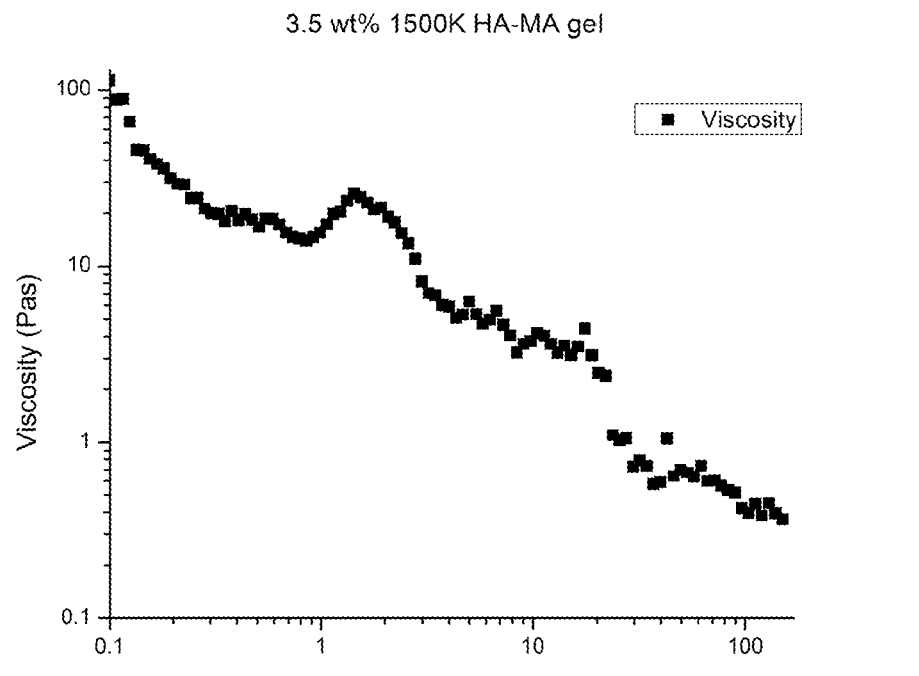
FIGS. 24(a)-24(b) show the rheology of another blended pHA-PEGDA ink system.
Figure 24B:
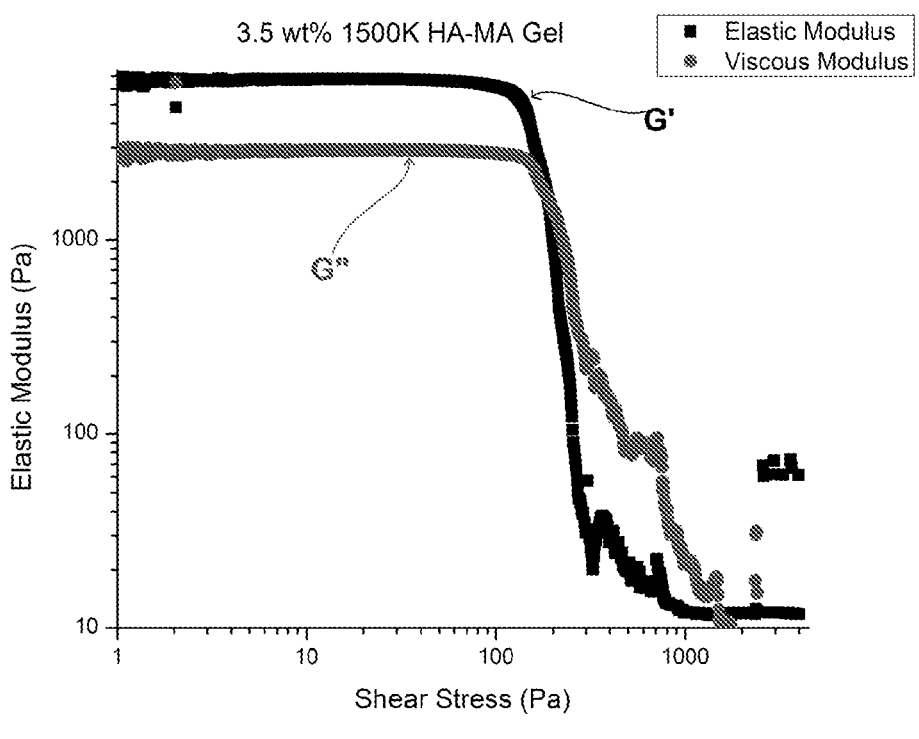
Figure 25:
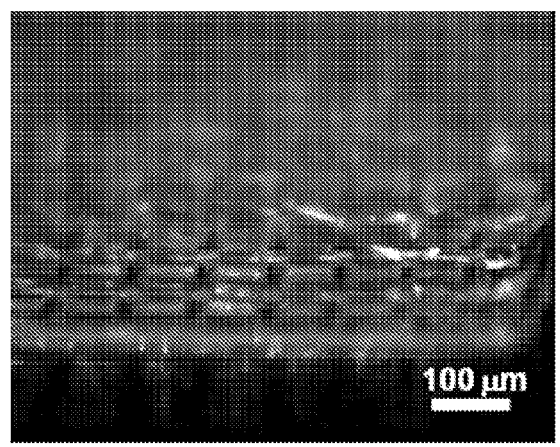
FIG. 25 is an optical micrograph showing the as-printed structure of the pHA-PEGDA system of FIGS. 24(a)-24(b) prior to UV exposure.
Figures 26A, 26B, 26C:
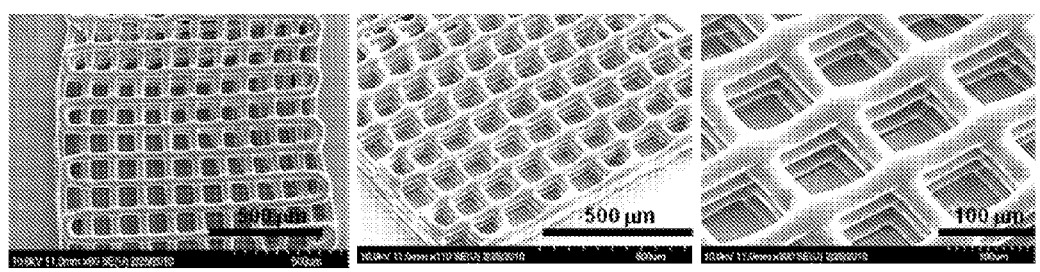
FIGS. 26(a)-26(c) are SEM images depicting the fabricated hydrogel scaffolds following UV exposure and drying of the as-printed structure of FIG. 25.
Figures 27A, 27B:
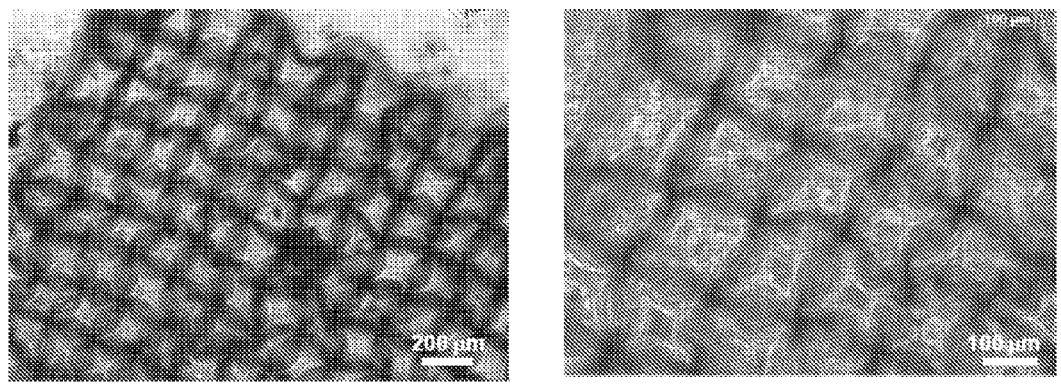
FIGS. 27(a)-27(b) show cell culture results after two days for the hydrogel scaffolds of FIGS. 26(a)-26(c).

FIGS. 24(a)-24(b) show the rheology of the Blended 2 ink system, and FIG. 25 is an optical micrograph showing the as-printed structure prior to UV exposure. FIGS. 26(a)-26(c) are SEM images depicting the fabricated hydrogel scaffolds following UV exposure and drying. Cell culture studies carried out with human embryonic stem cells (hESC) indicate that the cells incorporate into scaffold compartments. FIGS. 27(a)-27(b) show the cell culture results after two days.

A generic design for formulating and depositing viscoelastic inks that have dynamic and mechanical properties ideally

TABLE 1 pHA-Based Ink Systems.

| Component | Pure pHA | Blended 1 | Blended 2 |
|---|---|---|---|
| Poly(hyaluronic acid) (pHA) or methacrylated hyaluronic acid blend | 300 × 10$^3$ MW 10 wt. % | 300 × 10$^3$ MW 10 wt. % | 1.5 × 10$^6$ MW - 3.5 wt. % 300 × 10$^3$ MW - 10 wt. % |
| Polyethylene glycol diacrylate (PEGDA) | — | 700 MW 8 wt. % | 700 MW - 10 wt.% |
| Photoinitiator | Irgacure 2959 0.1 wt. % or Darocur 1173 1 wt. % | Irgacure 2959 0.1 wt. % | Irgacure 2959 - 0.1 wt. % |
| Surfactant | — | — | Tween 85 - 0.1 wt. % |
| Solvent | 50% Glycerol 50% Phosphate Buffered Saline (PBS) | 50% Glycerol 50% PBS | Glycerol - 39.2 wt. % PBS - 39.2 wt. % | suited for printing 3D structures has been described. Three model inks systems have been shown to have excellent 3D-writing capabilities and also cytocompatibility with several types of human cells. The ability to create hydrogel scaffolds with microscale features in both planar and 3D forms may open a new avenue for tailoring scaffolds for tissue engineering as well as other applications, including coatings, absorbent materials, surface modifications, extrusion molding, biomaterials, flexible electronics, photonics, rapid prototyping, and photopolymerizable materials.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A viscoelastic ink for direct writing of hydrogel structures, the ink comprising:
   a polymer;
   a photopolymerizable moiety;
   a photoinitiator; and
   water,
   wherein the polymer comprises poly(hyaluronic acid) (pHA), methacrylated hyaluronic acid or a blend of the two and is present at a concentration of about 5 wt. % or greater in the ink.

2. The ink of claim 1, wherein the photopolymerizable moiety is selected from the group consisting of: a photopolymerizable monomer; and a photopolymerizable group attached to the polymer.

3. A method for forming a hydrogel scaffold, the method comprising:
   forming an ink comprising a polymer and a photopolymerizable moiety, the polymer comprising poly(hyaluronic acid) (pHA), methacrylated hyaluronic acid or a blend of the two and being present at a concentration of about 5 wt. % or greater in the ink;
   extruding the ink through a micronozzle to form an extruded filament;
   photopolymerizing the extruded filament; and
   depositing the extruded filament in a pattern on a substrate to form a hydrogel scaffold,
   wherein the ink comprises a first viscosity at a low shear rate of about 0.1 $s^{-1}$ and a second viscosity during the extrusion, the second viscosity being at least about an order of magnitude lower than the first viscosity.

4. The method of claim 3, wherein the second viscosity is about 20 Pa·s or less.

5. The method of claim 3, wherein the photopolymerization of the extruded filament occurs prior to depositing the extruded filament on the substrate.

6. The method of claim 3, wherein the photopolymerization of the extruded filament occurs after depositing the extruded filament on the substrate.

7. The method of claim 3, further comprising, after the photopolymerization, chemically treating the hydrogel scaffold to render the scaffold compliant for tissue growth.

8. The method of claim 7, wherein chemically treating the scaffold comprises immersing the scaffold in a polylysine solution.

9. The method of claim 3, wherein the concentration of the polymer is between about 10 wt. % and about 50 wt. %.

10. The method of claim 3, wherein the photopolymerizable moiety comprises a photopolymerizable monomer present at a concentration of between about 25 wt. % and 55 wt. %.

11. The method of claim 3, wherein the photopolymerizable moiety comprises a photopolymerizable group attached to the polymer.

12. The method of claim 3, wherein, after photopolymerization, the extruded filament comprises a physically entangled polymer network and a chemically crosslinked polymer network.

13. The method of claim 3, wherein, after photopolymerization, the extruded filament comprises a chemically crosslinked polymer network with no physically entangled polymer chains.

14. The ink of claim 1, wherein the ink further comprises polyethylene glycol diacrylate (PEGDA).

15. The ink of claim 14, wherein the PEGDA is present at a concentration in the ink of up to about 10 wt. %.

16. The ink of claim 15, wherein the concentration of the pHA, the methacrylated hyaluronic acid, or said blend of the two is 10 wt. % and the concentration of the PEGDA is 8 wt. %.

17. The method of claim 3, wherein the ink further comprises polyethylene glycol diacrylate (PEGDA).

18. The method of claim 16, wherein the PEGDA is present at a concentration in the ink of up to about 10 wt. %.

19. The method of claim 18, wherein the concentration of the pHA, the methacrylated hyaluronic acid, or said blend of the two is 10 wt. % and the concentration of the PEGDA is 8 wt. %.

* * * * *